(12) United States Patent
Fujii

(10) Patent No.: US 11,839,353 B2
(45) Date of Patent: Dec. 12, 2023

(54) MEDICAL ENDOSCOPE DEVICE AND MEDICAL OBSERVATION SYSTEM

(71) Applicant: Sony Olympus Medical Solutions Inc., Tokyo (JP)

(72) Inventor: Daisuke Fujii, Hachioji (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 80 days.

(21) Appl. No.: 17/488,323

(22) Filed: Sep. 29, 2021

(65) Prior Publication Data
US 2022/0015608 A1 Jan. 20, 2022

Related U.S. Application Data

(63) Continuation of application No. 16/180,406, filed on Nov. 5, 2018, now abandoned.

(30) Foreign Application Priority Data

Dec. 7, 2017 (JP) .................. 2017-234812

(51) Int. Cl.
| | | |
|---|---|---|
| *A61B 1/00* | (2006.01) | |
| *A61B 1/04* | (2006.01) | |
| *H04N 19/13* | (2014.01) | |
| *H04N 19/174* | (2014.01) | |
| *H04N 19/65* | (2014.01) | |
| *H04N 19/136* | (2014.01) | |
| *H04N 19/172* | (2014.01) | |
| *H04N 19/115* | (2014.01) | |

(52) U.S. Cl.
CPC ...... *A61B 1/00016* (2013.01); *A61B 1/00009* (2013.01); *A61B 1/00029* (2013.01); *A61B 1/00048* (2013.01); *A61B 1/00188* (2013.01); *A61B 1/042* (2013.01); *H04N 19/115* (2014.11); *H04N 19/136* (2014.11); *H04N 19/172* (2014.11); *H04N 19/174* (2014.11); *H04N 19/65* (2014.11)

(58) Field of Classification Search
CPC .................................................. A61B 1/00009
USPC .......................................................... 348/65
See application file for complete search history.

(56) References Cited

U.S. PATENT DOCUMENTS

| | | | |
|---|---|---|---|
| 8,545,396 B2 | 10/2013 | Cover et al. | |
| 2005/0238255 A1* | 10/2005 | Niwa | ............... H04N 21/658 |
| | | | 375/E7.137 |
| 2013/0244580 A1 | 9/2013 | Yanagidate | |
| 2016/0112722 A1 | 4/2016 | Hogan | |
| 2017/0034484 A1 | 2/2017 | Yanagidate | |

(Continued)

FOREIGN PATENT DOCUMENTS

| | | |
|---|---|---|
| JP | 2004193683 A | 7/2004 |
| JP | 2005143668 A | 6/2005 |

(Continued)

*Primary Examiner* — Jeffery A Williams
(74) *Attorney, Agent, or Firm* — XSENSUS LLP

(57) ABSTRACT

There is provided a medical endoscope device including: an encoding processing unit configured to compression-encode RAW image data of a medical captured image of an observation target captured by an imaging device that is inserted into a body of a patient and captures an image of an inside of the body; and a transmission unit configured to wirelessly transmit the compression-encoded RAW image data.

21 Claims, 11 Drawing Sheets

(56) References Cited

U.S. PATENT DOCUMENTS

2018/0047165 A1    2/2018   Sato
2018/0220873 A1    8/2018   Tani

FOREIGN PATENT DOCUMENTS

| | | |
|---|---|---|
| JP | 2005159490 A | 6/2005 |
| JP | 2007098012 A | 4/2007 |
| JP | 2010-509990 A | 4/2010 |
| JP | 2010252276 A | 11/2010 |
| JP | 2014082705 A | 5/2014 |
| JP | 2014128423 A | 7/2014 |
| JP | 2016101377 A | 6/2016 |
| WO | WO-2013031156 | 3/2013 |
| WO | WO-2013069691 A1 | 5/2013 |
| WO | WO-2017061495 A1 | 4/2017 |

\* cited by examiner

MEDICAL ENDOSCOPE DEVICE AND MEDICAL OBSERVATION SYSTEM

CROSS-REFERENCE TO RELATED APPLICATIONS

This application is a continuation of U.S. application Ser. No. 16/180,406, filed Nov. 5, 2018, which claims priority to Japanese Patent Application No. 2017-234812, filed Dec. 7, 2017, the entire contents of each are incorporated herein by its reference.

BACKGROUND

The present disclosure relates to a medical endoscope device and a medical observation system.

In recent years, medical endoscope devices that enable observation targets such as affected areas to be enlarged and observed for performing endoscopic surgery have been used in medical sites. In this situation, technologies related to endoscope devices that wirelessly transmit images captured by imaging devices have been developed. As such a technology, for example, there is a technology disclosed in JP 2010-509990T.

SUMMARY

An operator, or the like who uses a medical endoscope device, for example, performs medical practice while viewing a display screen on which a medical captured image captured by the medical endoscope device is displayed. Thus, when a situation in which image data indicating the medical captured image is compression-encoded and the compression-encoded image data is transmitted in wireless communication is assumed, transmitting the image data with low latency is advantageous.

The present disclosure proposes a novel and improved medical endoscope device and medical observation system that enable image data indicating a compression-encoded medical captured image to be transmitted with low latency.

According to an embodiment of the present disclosure, there is provided a medical endoscope device including: an encoding processing unit configured to compression-encode RAW image data of a medical captured image of an observation target captured by an imaging device that is inserted into a body of a patient and captures an image of an inside of the body; and a transmission unit configured to wirelessly transmit the compression-encoded RAW image data.

In addition, according to an embodiment of the present disclosure, there is provided a medical reception device including: a reception unit configured to wirelessly receive compression-encoded RAW image data obtained by compression-encoding RAW image data of a medical captured image of an observation target captured by an imaging device that is inserted into a body of a patient and captures an image of an inside of the body; and a signal processing unit configured to process the received compression-encoded RAW image data.

In addition, according to an embodiment of the present disclosure, there is provided a medical observation system including: a medical endoscope device including an encoding processing unit configured to compression-encode RAW image data of a medical captured image of an observation target captured by an imaging device that is inserted into a body of a patient and captures an image of an inside of the body, and a transmission unit configured to wirelessly transmit the compression-encoded RAW image data; and a medical reception device including a reception unit configured to wirelessly receive the compression-encoded RAW image data, and a signal processing unit configured to process the received compression-encoded RAW image data.

According to an embodiment of the present disclosure, it is possible to transmit image data indicating a compression-encoded medical captured image with low latency.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
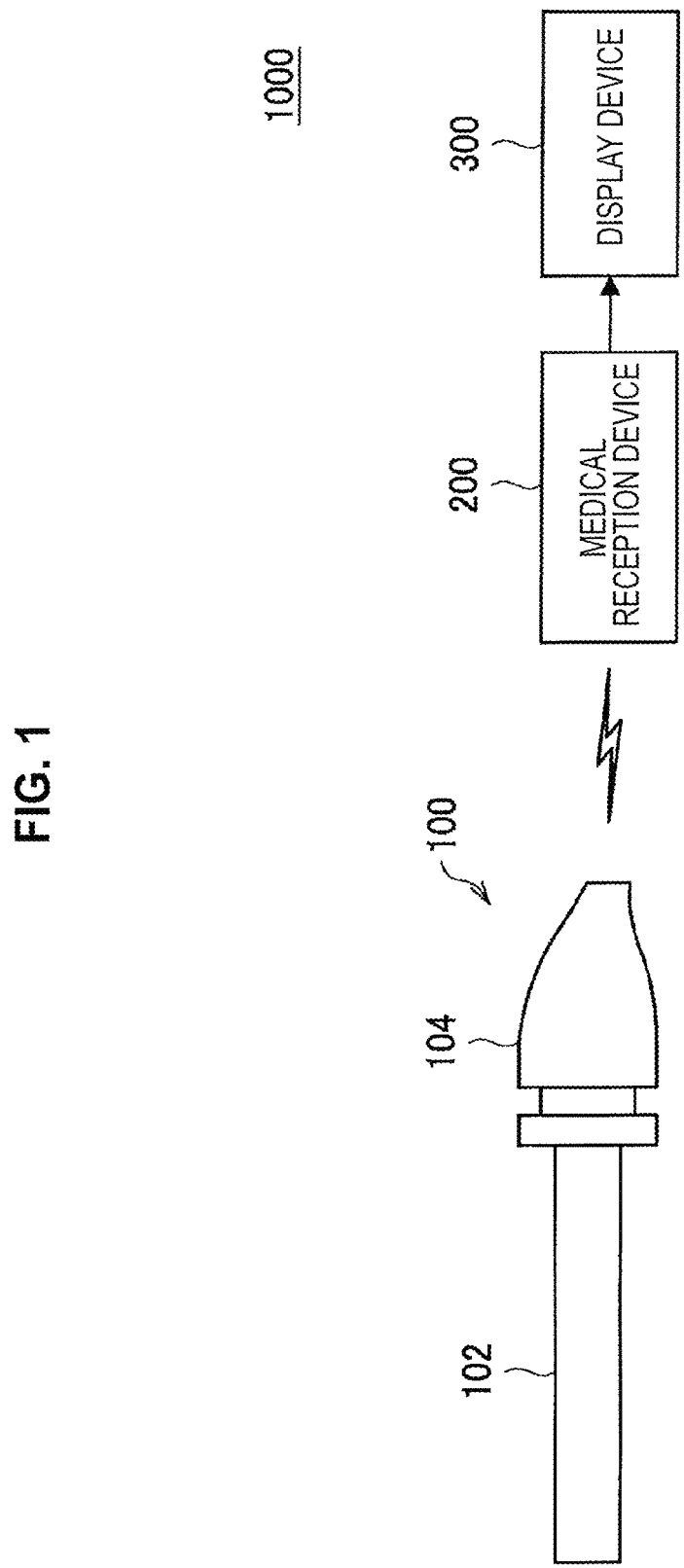
FIG. 1 is an explanatory diagram illustrating an example of a configuration of the medical observation system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

In addition, description will be provided in the following order below.
1. Medical observation system according to present embodiment
[1] Configuration of medical observation system
[2] Transmission method according to present embodiment
[3] Configurations of medical endoscope device and medical reception device according to present embodiment
[4] Example of effects exhibited when medical observation system according to present embodiment is used
2. Program according to present embodiment
(Medical Observation System According to Present Embodiment)
[1] Configuration of medical observation system FIG. 1 is an explanatory diagram illustrating an example of a configuration of a medical observation system 1000 according to the present embodiment of the present disclosure. The medical observation system 1000 illustrated in FIG. 1 has, for example, a medical endoscope device 100, a medical reception device 200, and a display device 300.

Note that the medical observation system according to the present embodiment is not limited to the example illustrated in FIG. 1.

The medical observation system according to the present embodiment may further have, for example, a control device (not illustrated) that controls various operations of the medical endoscope device 100. As the control device (not illustrated), for example, an arbitrary apparatus that can perform a process of a transmission method according to the present embodiment such as a "medical controller," or a "computer such as a server" is exemplified. In addition, the control device (not illustrated) may be, for example, an integrated circuit (IC) that can be incorporated into the above-described apparatus.

In addition, the medical observation system according to the present embodiment may have a plurality of "medical endoscope devices 100 and medical reception devices 200" and display devices 300. In the case in which a plurality of "medical endoscope devices 100 and medical reception devices 200" are included, each of the "medical endoscope devices 100 and medical reception devices 200" performs transmission using a transmission method which will be described below. In addition, in a case in which the medical observation system according to the present embodiment has a plurality of "medical endoscope devices 100 and medical reception devices 200" and display devices 300, the "medical endoscope devices 100 and medical reception devices 200" and the display devices 300 may be associated with each other one to one, or a plurality of "medical endoscope devices 100 and medical reception devices 200" may be associated with one display device 300. In the case in which a plurality of "medical endoscope devices 100 and medical reception devices 200" are associated with one display device 300, the display device 300 can switch the medical endoscope device 100 that has captured an image to be displayed on a display screen by performing, for example, a switching operation or the like.

In addition, the medical observation system according to the present embodiment may have a plurality of medical endoscope devices 100 associated with one medical reception device 200. In the case in which a plurality of medical endoscope devices 100 are associated with one medical reception device 200, the medical reception device 200 may switch the medical endoscope device 100 to perform wireless transmission therewith by performing, for example, a switching operation or the like.

In addition, the medical observation system according to the present embodiment may not have the display device 300. Even in the case in which the medical observation system according to the present embodiment does not have the display device 300, the medical observation system according to the present embodiment can transmit image data indicating a compression-encoded medical captured image with low latency using a transmission method according to the present embodiment which will be described below.

[1-1] Display Device 300

The display device 300 is a display section of the medical observation system 1000, and corresponds to an external display device with respect to each of the medical endoscope device 100 and the medical reception device 200. The display device 300 displays various images, for example, medical captured images (moving images or a plurality of still images; the same applies below) captured by the medical endoscope device 100, images relating to a user interface, and the like. In addition, the display device 300 may be capable of performing 3D display. Display by the display device 300 is controlled by, for example, the medical endoscope device 100, the medical reception device 200, or the control device (not illustrated).

The display device 300 of the medical observation system 1000 is installed in an arbitrary place at which the display device can be visually recognized by a person relating to surgery such as an operator within an operating room, for example, a wall surface, a ceiling, a floor of the operating room. As the display device 300, for example, a liquid crystal display, an organic electro-luminescence (EL) display, a cathode ray tube (CRT) display, or the like is exemplified.

Note that the display device 300 is not limited to the above-described example.

The display device 300 may be an arbitrary wearable device worn on the body of an operator or the like for use, for example, a head-mounted display, an eyewear-type device, or the like.

The display device 300 is driven by, for example, power supplied from an internal power supply included in the display device 300 such as a battery, power supplied from a connected external power supply, or the like.

[1-2] Medical Endoscope Device 100

The medical endoscope device 100 is a medical apparatus to be used in endoscopic surgery. The medical endoscope device 100 has the function of an endoscope and at least a function of transmitting signals wirelessly. In addition, the medical reception device 200 has at least a function of receiving signals transmitted from the medical endoscope device 100 wirelessly.

In a case in which the medical endoscope device 100 is used during surgery, an operator (an example of a user of the medical endoscope device 100) observes an operative site while referring to a medical captured image captured by the medical endoscope device 100 and being displayed on the display screen of the display device 300, and performs various treatments such as a procedure appropriate for the surgery type on the operative site.

The medical endoscope device 100 includes, for example, an insertion member 102, and a camera head 104. The medical endoscope device 100 is driven by, for example, power supplied from an internal power supply included in the medical endoscope device 100 such as a battery, power supplied from a connected external power supply, or the like.

The insertion member 102 has an elongated shape and includes an optical system that collects incident light. In addition, in a case in which the medical endoscope device 100 has a function of capturing stereoscopic images (medical captured images for the right eye and medical captured images for the left eye), for example, the insertion member 102 may include an optical system for capturing medical captured images for the right eye and an optical system for capturing medical captured images for the left eye.

The tip of the insertion member 102 is inserted into, for example, a body cavity of a patient. The rear end of the insertion member 102 is detachably connected to the tip of the camera head 104. In addition, the insertion member 102 receives supply of light from, for example, a light source provided in the camera head 104 or an external light source. In the case in which light is supplied from an external light source, the insertion member 102 is connected to the external light source via a light guide and receives supply of light from the external light source via the light guide.

The insertion member 102 may have, for example, a material having no flexibility or of a material having flexibility. The medical endoscope device 100 can be called a rigid endoscope or a flexible endoscope depending on a material forming the insertion member 102.

Light supplied to the insertion member 102 is injected from the tip of the insertion member 102 and radiated to an observation target such as a tissue in a body cavity of a patient. In addition, light reflected from the observation target is collected by the optical system inside the insertion member 102.

The camera head 104 includes, for example, an image sensor and has a function of capturing observation targets. The insertion member 102 and the camera head 104 of the medical endoscope device 100 play a role of, for example, an "imaging device that is inserted into the body of a patient and captures an image of the inside of the body."

In addition, the camera head 104 includes, for example, an encoding processing circuit and has a function of performing the processes of the transmission methods which will be described below.

In addition, the camera head 104 includes, for example, a transmitter and has at least a function of transmitting signals wirelessly. Note that the transmitter may be an external transmitter connected to the camera head 104.

A configuration example of the camera head 104 will be described below.

The medical endoscope device 100 has the function of an endoscope and at least the function of transmitting signals wirelessly since it includes, for example, the camera head 104 and the transmitter.

[1-3] Medical Reception Device 200

The medical reception device 200 includes, for example, a receiver and is a device having at least a function of receiving signals transmitted from the medical endoscope device 100 wirelessly.

In addition, the medical reception device 200 includes, for example, a signal processing circuit and has a function of processing signals received by the receiver. In one example of signal processing of the signal processing circuit, the signal processing circuit performs, for example, a decoding process of decoding compression-encoded image data. In addition, the signal processing circuit may perform various kinds of processing that can be performed on medical captured images, for example, a demosaic process for adjusting RAW image data (e.g., arbitrary processing for adjusting color, brightness, and the like based on RAW image data; the same applies below), enlargement or reduction of images relating to an electronic zoom function, inter-pixel correction, and the like.

In addition, the medical reception device 200 may include, for example, a communication device and have a function of controlling display of the display device 300. For example, the medical reception device 200 transmits image data processed by the signal processing circuit and a display control signal to the display device 300 through the communication device (not illustrated) and thereby controls display of the display device 300.

As the communication device included in the medical reception device 200, for example, an IEEE 802.15.1 port and a transmission/reception circuit (wireless communication), an IEEE 802.11 port and a transmission/reception circuit (wireless communication), a communication antenna and a radio frequency (RF) circuit (wireless communication), an optical communication device (wired communication or wireless communication), a local area network (LAN) terminal and a transmission/reception circuit (wired communication), or the like are exemplified. The communication device may be capable of communicating with one or two or more external devices using a plurality of communication methods.

Note that functions of the medical reception device 200 are not limited to the above-described examples. The medical reception device 200 can have various functions, for example, a function of recording a medical captured image based on image data processed by the signal processing circuit in an arbitrary recording medium, and the like.

An example of a configuration of the medical reception device 200 will be described below.

[2] Transmission Method According to Present Embodiment

[2-1] Overview of Transmission Methods According to Present Embodiment

In medical endoscope devices of recent years, amounts of image data indicating medical captured images have tended to increase resulting from, for example, high resolution of imaging devices, high frame rates, stereoscopy, mounting of additional devices for observing special light incident on the imaging devices, and the like. Image data indicating a medical captured image may be simply referred to as "image data" below.

When amounts of image data increases as described above, power consumption of the medical endoscope device increases accordingly. In addition, since an amount of heat generation increases due to the increase of power consumption, the sizes of members (e.g., the size of the camera head constituting the endoscope device) constituting the medical observation device should be increased in order to deal with heat. Therefore, an increase in amounts of image data is disadvantageous for miniaturizing the medical endoscope device.

Here, as a first method of reducing amounts of image data, compression-encoding of the image data is conceivable.

Figure 2:
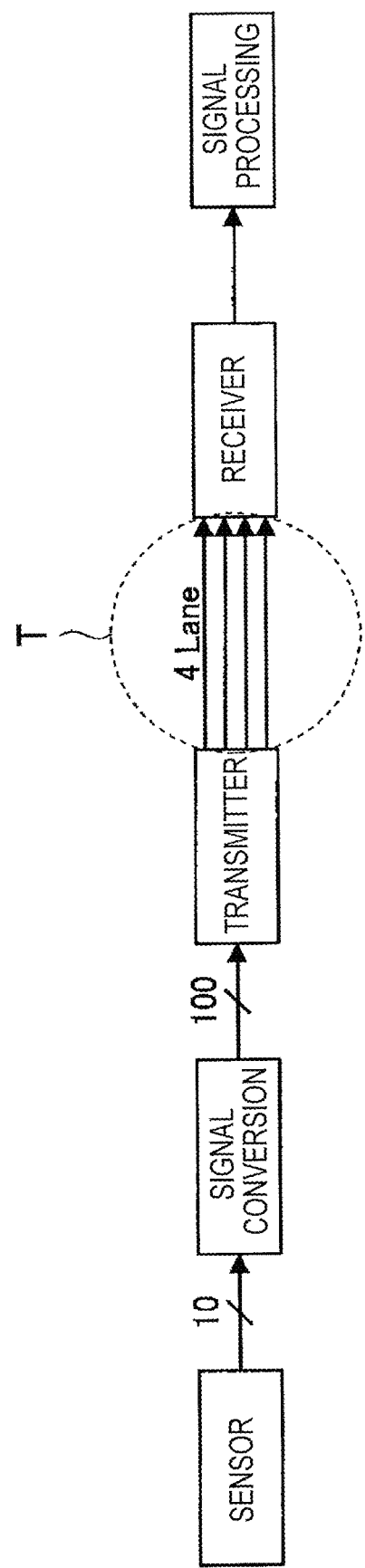
FIG. 2 is an explanatory diagram illustrating an example of transmission of image data indicating a medical captured image in a case in which the image data is not compression-encoded.
Figure 3:
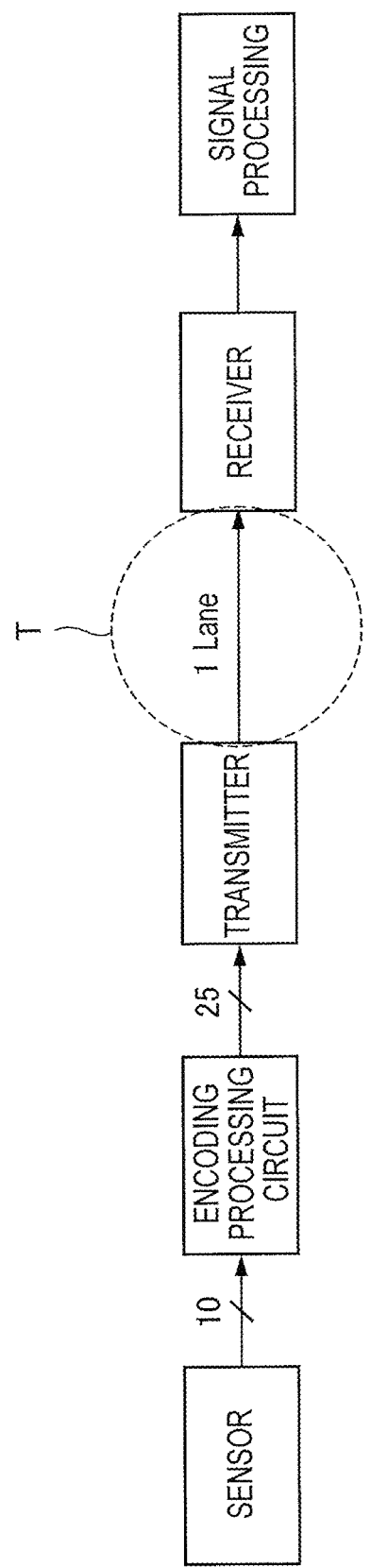
FIG. 3 is an explanatory diagram illustrating an example of transmission of image data indicating a medical captured image in a case in which the image data is compression-encoded.

FIG. 2 is an explanatory diagram illustrating an example of transmission of image data indicating a medical captured image in a case in which the image data is not compression-encoded. In addition, FIG. 3 is an explanatory diagram illustrating an example of transmission of image data indicating a medical captured image in a case in which the image data is compression-encoded. In FIGS. 2 and 3, image sensors included in the imaging devices are denoted by "sensor." In addition, in FIGS. 2 and 3, transmitters are denoted by "TX," and receivers are denoted by "RX."

In the case in which image data indicating a medical captured image is not compression-encoded, for example, the image data is transmitted from the transmitter to the receiver on a 4-lane communication path T as illustrated in FIG. 2.

On the other hand, in a case in which image data indicating a medical captured image is compression-encoded at a compression ratio of 1/4, the compression-encoded image data is transmitted from the transmitter to the receiver on one lane of the communication path T, for example, as illustrated in FIG. 3. In addition, in a case in which image data is compression-encoded at a compression ratio of 1/8, the image data indicating a medical captured image functioning as a stereo image can be transmitted on one lane of the communication path T.

By compression-encoding the image data as illustrated in FIG. 3, for example, the amount of the image data can be reduced in accordance with the compression ratio and degradation of the quality of the decoded medical captured image can be prevented.

In addition, as a second method of reducing amounts of image data, transmitting RAW image data of a medical captured image captured by an imaging device is conceivable. RAW image data according to the present embodiment is, for example, image data that has yet to undergo a demosaic process.

Here, as advantages of transmitting RAW image data, for example, advantages described in (A) and (B) below are exemplified.

(A) First Advantage of Transmitting RAW Image Data

A transmission amount can be reduced in a case in which RAW image data is transmitted more than in a case in which demosaic-processed image data is transmitted as will be shown in the following example. In addition, since an amount of RAW image data is smaller than when it has undergone a general demosaic process (YCbCr=4:2:2), a load of compression and transmission becomes smaller, and as a result, transmission with low latency occurs.

A transmission amount in a case in which 4K RAW data (in a Bayer array, 10 [bits], and a frame rate of 59.94 [p]) is transmitted with no compression: about 5.3 [Gbps]

A transmission amount in a case in which demosaic-processed data with YCbCr=4:2:2 (of 10 [bits], and a frame rate of 59.94 [p]) is transmitted with no compression: about 10 [Gbps]

That is, when RAW data (in a Bayer array) is compared with general demosaic-processed data (with YCbCr=4:2:2), the RAW data (of the Bayer array) can have about half (about 0.5 times) the transmission rate thereof. Thus, when it is assumed that RAW image data (in a Bayer array) and general demosaic-processed image data (with YCbCr=4:2: 2) are compressed and transmitted under a similar condition, the RAW image data (in Bayer array) can realize a lower transmission rate with higher image quality or higher quality.

Here, by realizing a lower transmission rate with higher image quality, for example, transmission with high image quality is possible even with devices of low transmission rates. In addition, by realizing a lower transmission rate with high quality, for example, the marginal portion of transmission can be redirected to stable wireless transmission (robust optimization).

(B) Second Advantage of Transmitting RAW Image Data

RAW image data is image data of which information of light at the time of imaging is retained inside the imaging device as it is without adjustment, that is, pre-processed image data that has not undergone a demosaic process or the like. Thus, by transmitting RAW image data, a device on the reception side can perform adjustment of hue, brightness, and the like without degrading the image quality, and can adjust exposure and white balance later. In addition, the device on the reception side can perform an arbitrary demosaic process and processing on the RAW image data.

Thus, in the medical observation system 1000, the medical endoscope device 100 compression-encodes RAW image data indicating a medical captured image and wirelessly transmits the compression-encoded RAW image data. That is, in the medical observation system 1000, the medical endoscope device 100 performs compression-encoding on RAW image data without performing the demosaic process. In the medical observation system 1000, the demosaic process is performed by the medical reception device 200 as will be described below. RAW image data indicating a medical captured image is sometimes referred to simply as "RAW image data" below.

When compression-encoded RAW image data is transmitted wirelessly, both the effect exhibited by using the first method of reducing an amount of the image data and the effect exhibited by using the second method of reducing an amount of the image data are exhibited.

Thus, the medical observation system 1000 realizes transmission of compression-encoded image data indicating a medical captured image with lower latency.

Here, when compression-encoding RAW image data indicating a medical captured image and then transmitting the compression-encoded RAW image data in wireless communication is assumed, it may be necessary to further reduce the influence of an error caused by the compression-encoding.

Therefore, next, an example of a compression-encoding method according to the present embodiment to be applied to the medical endoscope device 100 will be described. Note that it is a matter of course that a compression-encoding method to be applied to the medical endoscope device 100 is not limited to the following example.

Figure 4:
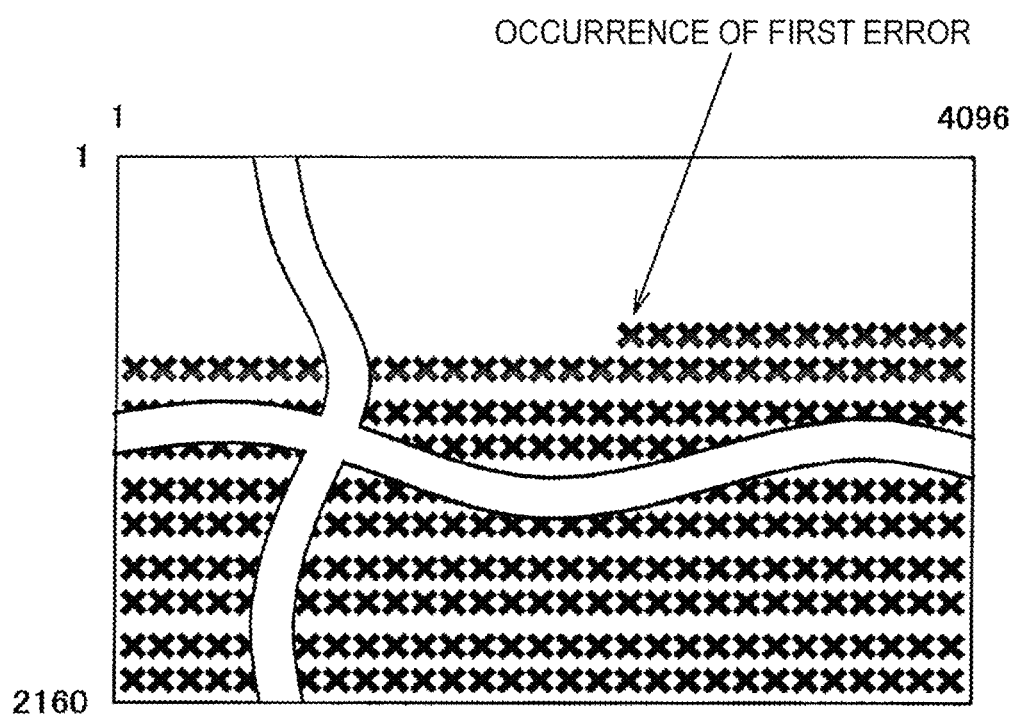
FIG. 4 is an explanatory diagram for describing an example of an error caused by compression-encoding.

FIG. 4 is an explanatory diagram for describing an example of an error caused by compression-encoding. FIG. 4 conceptually illustrates an error occurring in a case in which an entire medical captured image with 4K resolution (4096×2160 pixels) of a certain frame (an example of an entire frame image) is compression-encoded.

In the case in which the entire medical captured image is compression-encoded as illustrated in, for example, FIG. 4, when an error occurs in the course of compression-encoding, it is not possible to decode pixels from the pixel at which the error occurs to the final pixel of the frame to be processed after the occurrence of the error. That is, in the case in which the entire medical captured image is compression-encoded, the influence of the error occurring in the course of the compression-encoding is propagated to all pixels processed after the occurrence of the error.

Thus, the medical endoscope device 100 compression-encodes the RAW image data indicating a medical captured image by each predetermined unit that is smaller than the medical captured image.

As the predetermined unit according to the present embodiment, for example, the unit of a plurality of lines of the medical captured image, such as every 16 lines, is exemplified. Here, the predetermined unit may be a preset fixed unit or a variable unit that can be changed on the basis of an operation of a user using the medical observation system 1000, an operation state of a predetermined medical apparatus, or the like.

Note that the predetermined unit according to the present embodiment is not limited to a unit of a plurality of lines of a medical captured image. The predetermined unit according to the present embodiment may be, for example, a block unit that includes a plurality of pixels and is smaller than the entire medical captured image. Hereinbelow, a case in which the predetermined unit according to the present embodiment is a unit of a plurality of lines of a medical captured image will be exemplified. In addition, hereinbelow, the predetermined unit defined as a unit of a plurality of lines of a medical captured image may be indicated as a "slice unit."

Figure 5:
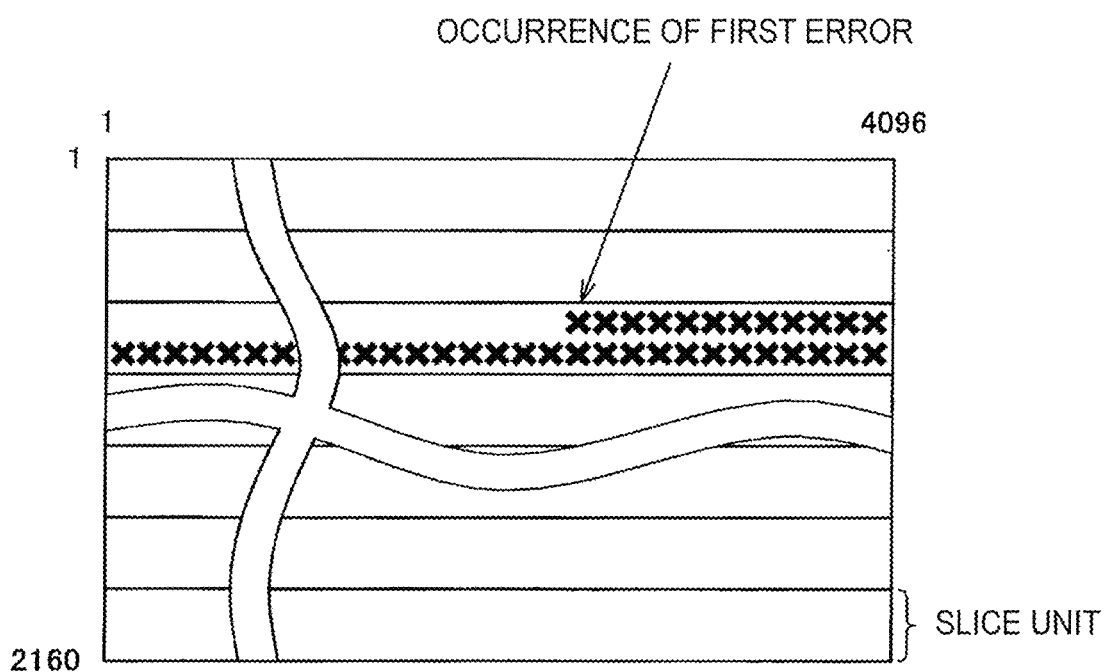
FIG. 5 is an explanatory diagram for describing an example of an error caused by compression-encoding in a case in which a compression-encoding method according to an embodiment of the present disclosure is applied.

FIG. 5 is an explanatory diagram for describing an example of an error caused by compression-encoding in a case in which the compression-encoding method according to the present embodiment is applied. FIG. 5 conceptually illustrates an error occurring in a case in which an entire medical captured image of 4K resolution of a certain frame is compression-encoded, as in FIG. 4.

In a case in which a medical captured image is compression-encoded by a slice unit (an example of a predetermined unit), for example, as illustrated in FIG. 5, even if an error occurs in the course of the compression-encoding, propagation of the error stops at a slice unit in which the error has occurred, and the influence thereof does not spread to slice units processed thereafter.

Therefore, the medical endoscope device 100 can reduce the amount of the RAW image data while further reducing the influence of the error caused by the compression-encoding by compression-encoding the RAW image data using the compression-encoding method according to the present embodiment.

In addition, in a case in which the medical captured image is compression-encoded by a smaller predetermined unit, for example, like the slice unit as illustrated in FIG. 5, the time taken to perform compression-encoding by the predetermined unit becomes shorter than in the case in which the entire medical captured image is compression-encoded as illustrated in FIG. 4. Therefore, in the case in which the compression-encoding method according to the present embodiment is used, the compression-encoded RAW image data can be transmitted with lower latency than in the case in which the entire medical captured image is compression-encoded as illustrated in FIG. 4. In addition, such transmission of image data with low latency is beneficial when medical staff performing medical practice while viewing a decoded medical captured image are taken into account.

[3] Configurations of Medical Endoscope Device and Medical Reception Device According to Present Embodiment Next, examples of configurations of the medical endoscope device and the medical reception device according to the present embodiment to which the above-described transmission methods according to the present embodiment can be applied will be described. Note that examples of configurations of the medical endoscope device and the medical reception device according to the present embodiment are not limited to the following examples. For example, each of the medical endoscope device and the medical reception device according to the present embodiment may also employ a configuration obtained by combining the following examples.

Figure 6:
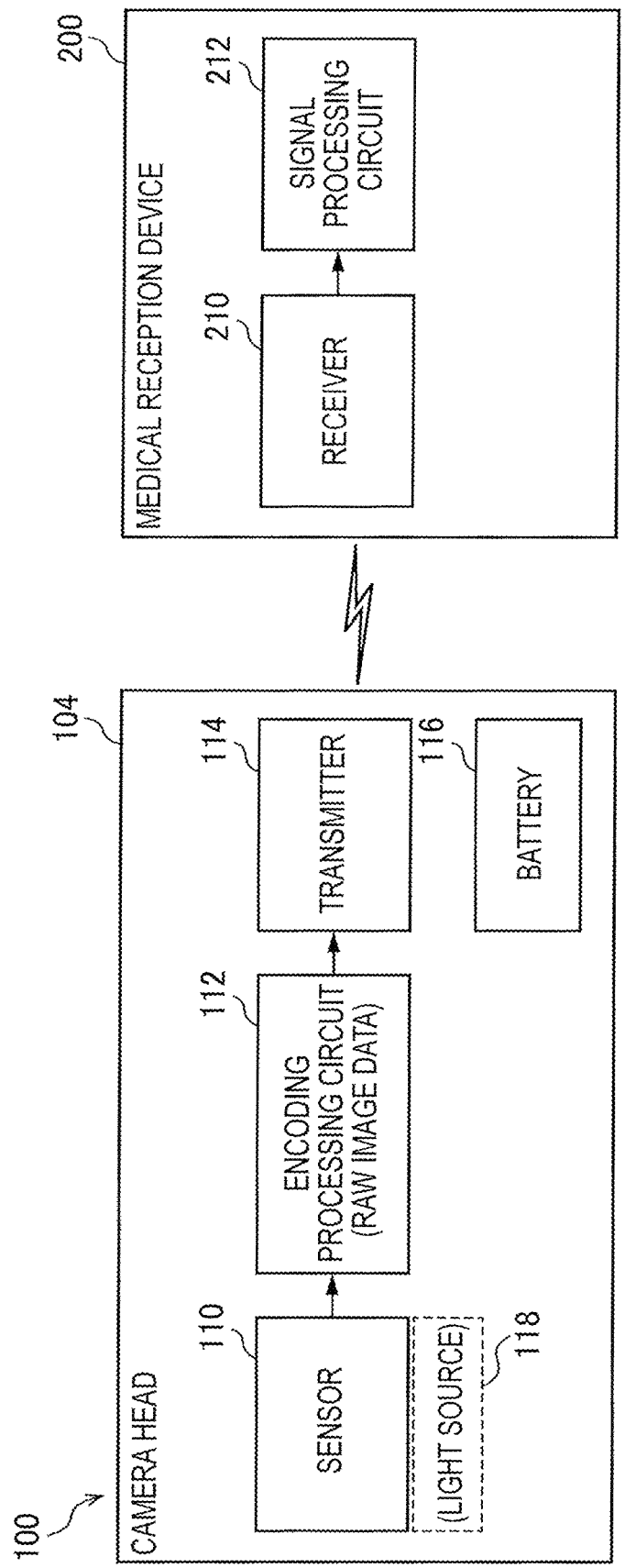
FIG. 6 is a diagram of hardware blocks illustrating an example of a configuration of a medical endoscope device and a medical reception device according to a first embodiment of the present disclosure.

[3-1] Configurations of Medical Endoscope Device and Medical Reception Device According to First Embodiment FIG. 6 is a diagram of hardware blocks illustrating an example of a configuration of the medical endoscope device 100 and the medical reception device 200 according to a first embodiment of the present disclosure. Note that, in FIG. 6, the hardware configuration of the camera head 104 that performs the processes of the transmission methods according to the present embodiment out of the hardware configuration of the medical endoscope device 100 is illustrated.

[3-1-1] Configuration of Medical Endoscope Device 100 According to First Embodiment The camera head 104 included in the medical endoscope device 100 includes, for example, a sensor 110, an encoding processing circuit 112, a transmitter 114, a battery 116, and a light source 118.

In addition, the camera head 104 may further include, for example, a recording medium (not illustrated) on which data to be used by the encoding processing circuit 112 in processing is recorded. As the recording medium (not illustrated), for example, a flash memory, a read only memory (ROM), or the like is exemplified. Note that the recording medium (not illustrated) may be included in another constituent element included in the camera head 104, such as the encoding processing circuit 112. In addition, the recording medium (not illustrated) may be an external recording medium of the medical endoscope device 100.

[3-1-1-1] Sensor 110

Each of the sensor 110, the encoding processing circuit 112, the transmitter 114, and the light source 118 is electrically connected to the battery 116 (an example of an internal power supply) and operates with power supplied from the battery 116. As the battery 116, for example, a secondary battery such as a lithium-ion secondary battery or the like is exemplified.

The sensor 110 images an observation target by photo-electrically converting light reflected from the observation target collected by the insertion member 102 and transfers RAW image data obtained from the imaging (RAW image data indicating a medical captured image) to the encoding processing circuit 112. As the sensor 110, for example, an image sensor in which a plurality of image sensor elements such as complementary metal oxide semiconductors (CMOSs) or charge coupled devices (CCDs) are used is exemplified.

In addition, for example, in a case in which the insertion member 102 includes two optical systems (an optical system for capturing medical captured images for the right eye and an optical system for capturing medical captured images for the left eye), the sensor 110 transfers first RAW image data of a medical captured image for the right eye and second RAW image data of a medical captured image for the left eye to the encoding processing circuit 112.

[3-1-1-2] Encoding Processing Circuit 112

The encoding processing circuit 112 is a circuit functioning as an encoding processing unit of the medical endoscope device 100 and compression-encodes RAW image data. The encoding processing circuit 112 performs, for example, a process of the compression-encoding method according to the present embodiment and compression-encodes RAW image data by each predetermined unit that is smaller than a medical captured image.

Note that a process of the encoding processing circuit 112 is not limited to the above example. The encoding processing circuit 112 may perform, for example, a process of a first example introduced in (1) and a process of a fifth example introduced in (5) below.

(1) First Example of Process of Encoding Processing Circuit 112

The encoding processing circuit 112 compression-encodes RAW image data at a plurality of different compression ratios. Since the encoding processing circuit 112 compression-encodes RAW image data at a plurality of different compression ratios, the medical endoscope device 100 obtains a plurality of pieces of RAW image data compressed at different compression ratios.

(2) Second Example of Process of Encoding Processing Circuit 112

The encoding processing circuit 112 performs compression-encoding at a compression ratio corresponding to a state of electronic zoom of the imaging device.

Electronic zoom of the medical endoscope device 100 is a zoom method of changing a zoom magnification by performing image processing on a medical captured image, for example, without moving a lens included in the optical system of the insertion member 102. Image processing on medical captured images for electronic zoom, such as enlarging an image by appropriately performing various processes like an interpolation process, is performed by a reception side device, for example, the medical reception device 200, or the like.

In a case in which electronic zoom is performed, there is no need to physically move a zoom lens included in the optical system, unlike in a case in which optical zoom is performed, zoom magnifications are changed through image processing, and thus zoom magnifications are discontinuously changed. Thus, in the case in which electronic zoom is performed, there is an advantage that zoom can be discontinuously changed to a desired zoom magnification within a shorter time than in the case in which optical zoom is performed.

In the case in which electronic zoom is performed, the encoding processing circuit 112 cuts out a partial region of a medical captured image and then compression-encodes RAW image data corresponding to the cut-out region at a compression ratio corresponding to the state of electronic zoom.

A compression ratio corresponding to the state of electronic zoom is determined on the basis of, for example, one or both a size of the cut-out region and a magnification of the electronic zoom.

A size of the cut-out region and a magnification of the electronic zoom are acquired from an external device, for example, the medical reception device 200, an external operation device such as a remote controller, or the like. Data indicating a size of the cut-out region and data indicating a magnification of the electronic zoom can be received using, for example, a reception function of the transmitter 114, which will be described below. That is, the transmitter 114 can function also as a receiver for the camera head 104. Note that it is a matter of course that the camera head 104 may further include a receiver that can receive signals transmitted from the outside.

To exemplify a case in which a compression ratio is determined on the basis of a size of the cut-out region and a magnification of the electronic zoom, the encoding processing circuit 112 determines a compression ratio by referring to, for example, a "table (or database) in which sizes of cut-out regions, magnifications of electronic zoom, and compression ratios are associated with each other" which is stored in a recording medium (not illustrated). Note that the encoding processing circuit 112 may determine a compression ratio corresponding to one or both of a size of the cut-out region and a magnification of the electronic zoom by performing, for example, an arithmetic operation of an arbitrary algorithm with which a compression ratio can be determined in accordance with one or both of the size of the cut-out region and the magnification of the electronic zoom.

To give a specific example, the encoding processing circuit 112 compression-encodes RAW image data at a compression ratio of 1/4 since the data amount becomes 1/4 when the magnification of electronic zoom is two times. In addition, it is also possible for the encoding processing circuit 112 not to compression-encode RAW image data in accordance with a size of the cut-out region or a combination of a size of the cut-out region and a magnification of the electronic zoom.

(3) Third Example of Process of Encoding Processing Circuit 112

In a case in which first RAW image data of a medical captured image for the right eye and second RAW image data of the medical captured image for the left eye are transferred from the sensor 110, the encoding processing circuit 112 compression-encodes each of the first RAW image data and the second RAW image data.

(4) Fourth Example of Process of Encoding Processing Circuit 112

When a place in which the medical observation system 1000 is used, such as the field of surgery, is assumed, for example, wireless transmission states are likely to be affected by the following factors:

Noise of a transmitting apparatus (noise of both a transmission side apparatus and a reception side apparatus);

Interference of noise emanated from a treatment device such as an electrical scalpel or bipolar forceps;

Interference of electromagnetic noise emanated from light emitting diode (LED) lighting equipment, various distribution cables for distributing satellite broadcasting and the like, a clinical sensor, an access point of a wireless LAN (base station), a telemeter telecontroller, a nurse call input/output (I/O), or the like;

Radio interference or the like that occurs when the same channel (same frequency) is used in close places;

Weak (low) radio wave intensity;

Separation distance between antennas (e.g., the limit of the separation distance is about 100 m for IEEE 802.11ac (5 GHz) and about 10 m for IEEE 802.11ad (60 GHz)); and Physical shield between antennas (e.g., radio waves at a high frequency level of IEEE 802.11ad (60 GHz) do not go through when shielded by a metallic object, a human, or the like).

Thus, the encoding processing circuit 112 can change a way of compression-encoding of RAW image data on the basis of a wireless transmission state.

The following, for example, are examples of changing a way of compression-encoding by the encoding processing circuit 112. Note that it is a matter of course that examples of changing a way of compression-encoding by the encoding processing circuit 112 are not limited to the following examples.

Changing a compression ratio to one corresponding to a wireless transmission state Changing a predetermined unit to a unit corresponding to a wireless transmission state Switching whether an error correction code is to be added in accordance with a wireless transmission state A combination of two or more of the above The encoding processing circuit 112 specifies a way of compression-encoding in accordance with a wireless transmission state by referring to, for example, a "table (or database) in which wireless transmission states are associated with data indicating a way of compression-encoding" stored in a recording medium (not illustrated). In addition, the encoding processing circuit 112 may specify a way of compression-encoding in accordance with a wireless transmission state by performing, for example, an arithmetic operation of an arbitrary algorithm with which a way of compression-encoding can be determined in accordance with a wireless transmission state.

Then, the encoding processing circuit 112 compression-encodes RAW image data in the specified way of compression-encoding in accordance with the wireless transmission state.

By changing a way of compression-encoding in accordance with a wireless transmission state as described above, for example, switching to a way with stronger error resistance is realized while taking a transmission environment into account.

The encoding processing circuit 112 specifies a wireless transmission state, for example, on the basis of a result of bidirectional communication with the medical reception device 200 and thus changes a way of compression-encoding of RAW image data. Bidirectional communication with the medical reception device 200 is realized by, for example, the transmitter 114, which will be described below, having the reception function. Note that it is a matter of course that the camera head 104 may further include a receiver that can receive signals transmitted from the outside as described above.

To give a specific example, the encoding processing circuit 112 acquires a transmission amount (transmission speed) using a wireless transmission protocol (e.g., a transmission of a ping command, a response to a ping command, and the like) and specifies a transmission state corresponding to the transmission amount. Then, the encoding processing circuit 112 compression-encodes RAW image data in a way of compression-encoding in accordance with the specified wireless transmission state. A transmission state corresponding to the transmission amount is determined by referring to, for example, a "table (or database) in which transmission amounts are associated with compression ratios" stored in a recording medium (not illustrated). Note that the encoding processing circuit 112 may specify a transmission state corresponding to the transmission amount by performing, for example, an arithmetic operation of an arbitrary algorithm with which a transmission state can be determined in accordance with the transmission amount.

Note that a specification method for a wireless transmission state is not limited to the above-described example.

For example, the encoding processing circuit 112 can also specify a transmission state on the basis of the comparison result of a set reference value and an actual transmission value of the transmitter 114 and thus change a way of compression-encoding of RAW image data.

To give a specific example, when a reference value is set to a value a [bps] indicating a transmission speed and an actual transmission value is set to b [bps], the encoding processing circuit 112 obtains a transmission rate by performing an arithmetic operation using, for example, the following formula 1.

$$\text{Transmission rate [\%]}=(b/a)\times 100 \quad \text{Formula 1}$$

Then, the encoding processing circuit 112 changes a way of compression-encoding of RAW image data using the obtained transmission rate.

To give a specific example, in a case in which a=400 [Mbps] and b=100 [Mbps], the encoding processing circuit 112 obtains the transmission rate=25 [%] through the above formula 1. Here, the transmission rate 25 [%] means that the transmission speed is only a quarter of the expected value. Thus, the encoding processing circuit 112 can change a way of compression-encoding of RAW image data by setting, for example, the compression ratio to quadruple or the like.

(5) Fifth Example of Process of Encoding Processing Circuit 112

The encoding processing circuit 112 may perform two or more processes to be combined among the process of the first example introduced in (1) to the process of the fourth example introduced in (4) above.

[3-1-1-3] Transmitter 114

The transmitter 114 is a circuit that functions as a transmission unit in the medical endoscope device 100 and wirelessly transmits compression-encoded RAW image data transferred from the encoding processing circuit 112.

As the transmitter 114, a communication device compatible with wireless communication in an arbitrary communication method, for example, an IEEE 802.15.1 port and a transmission/reception circuit, an IEEE 802.11 port and a transmission/reception circuit, a communication antenna and an RF circuit, an optical communication device (for wireless communication), or the like is exemplified. The transmitter 114 can have the function of a receiver as described above. In addition, the transmitter 114 includes a processor, and also can perform a process relating to an operation, which will be described below, with the process.

Note that, the medical endoscope device 100 can also include a communication device compatible with wired communication in an arbitrary communication method such as an optical communication device (for wired communication) or a LAN terminal and a transmission/reception circuit, as will be described below.

Note that an operation of the transmitter 114 is not limited to the above-described example. The transmitter 114 may perform, for example, an operation of a first example introduced in (i) to an operation of a fifth example introduced in (v) below.

(i) First Example of Operation of Transmitter 114

In a case in which the encoding processing circuit 112 performs the process of the first example introduced in (1) above, that is, in a case in which RAW image data is compression-encoded at a plurality of different compression ratios, the transmitter 114 transmits compression-encoded RAW image data corresponding to a wireless transmission state of the RAW image data compression-encoded at the plurality of compression ratios.

Through the operation of the first example performed by the transmitter 114, the medical endoscope device 100 realizes, for example, 1037 transmission performed such that transmission of data with low compression is prioritized and it is switched to transmission of data with high compression when a wireless transmission state is bad. In addition, by switching from transmission of data with low compression into transmission of data with high compression in accordance with a wireless transmission state as described above, the medical observation system 1000 maintains the transmission state of RAW image data with low latency even in a case in which a transmission rate deteriorates.

Here, the wireless transmission state is specified by, for example, the encoding processing circuit 112 as described above. Note that the wireless transmission state may be specified by the transmitter 114.

In a case in which only compression-encoded RAW image data corresponding to the wireless transmission state of the RAW image data compression-encoded by the encoding processing circuit 112 at the plurality of compression ratios is transferred from the encoding processing circuit 112, for example, the transmitter 114 wirelessly transmits the compression-encoded RAW image data transferred from the encoding processing circuit 112.

In addition, in a case in which RAW image data compression-encoded at the plurality of compression ratios is transferred from the encoding processing circuit 112, the transmitter 114 selects compression-encoded RAW image data corresponding to the wireless transmission state from the transferred compression-encoded RAW image data and wirelessly transmits the selected compression-encoded RAW image data.

(ii) Second Example of Operation of Transmitter 114

The transmitter 114 transmits compression-encoded RAW image data at different frequencies.

More specifically, the transmitter 114 transmits, for example, compression-encoded RAW image data at different frequencies at the same time. By transmitting compression-encoded RAW image data at different frequencies at the same time, a possibility of the medical reception device 200 being able to receive the compression-encoded RAW image data can be raised.

In addition, the transmitter 114 may transmit the compression-encoded RAW image data at, for example, any one frequency of the plurality of frequencies.

To give an example, the transmitter 114 transmits compression-encoded RAW image data at a frequency corresponding to a wireless transmission state. By transmitting compression-encoded RAW image data at a frequency corresponding to a wireless transmission state among a plurality of frequencies, the medical endoscope device 100 can transmit the compression-encoded RAW image data more stably while further reducing power consumption for the transmission of the compression-encoded RAW image data.

To give another example, the transmitter 114 can also transmit compression-encoded RAW image data at a frequency corresponding to an operation state of a predetermined medical apparatus. As a predetermined medical apparatus according to the present embodiment, for example, a treatment device such as an electrical scalpel or bipolar forceps is exemplified.

In a case in which a predetermined medical apparatus operates, there is a possibility of a generated electric field affecting communication between the transmitter 114 and a receiver (which will be described below) included in the medical reception device 200 depending on an operation state of the predetermined medical apparatus.

Thus, the transmitter 114 performs transmission at a frequency corresponding to an operation state of a predetermined medical apparatus. An operation state of a predetermined medical apparatus is acquired through, for example, communication with another predetermined medical apparatus (or a control device controlling the predetermined medical apparatus).

The transmitter 114 specifies a frequency for an operation state of the predetermined medical apparatus by referring to, for example, a "table (or database) in which operation states of predetermined medical apparatuses are associated with frequencies" stored in a recording medium (not illustrated). In addition, the transmitter 114 may specify a frequency for an operation state of the predetermined medical apparatus by performing, for example, an arithmetic operation of an arbitrary algorithm with which a frequency can be determined in accordance with an operation state of a predetermined medical apparatus.

By transmitting the compression-encoded RAW image data at a frequency corresponding to an operation state of the predetermined medical apparatus among the plurality of frequencies, the medical endoscope device 100 can transmit the compression-encoded RAW image data more stably while further reducing power consumption for the transmission of the compression-encoded RAW image data.

To give another example, the transmitter 114 can also transmit compression-encoded RAW image data at a frequency corresponding to a wireless transmission state and an operation state of a predetermined medical apparatus.

(iii) Third Example of Operation of Transmitter 114

In a case in which the encoding processing circuit 112 performs the process of the third example introduced in (3) described above, that is, "a case in which compression-encoded first RAW image data of a medical captured image for the right eye and compression-encoded second RAW image data of a medical captured image for the left eye are transferred from the encoding processing circuit 112," the transmitter 114 wirelessly transmits each of the compression-encoded first RAW image data and the compression-encoded second RAW image data.

Note that an operation of the transmitter 114 in a case in which the encoding processing circuit 112 performs the process of the third example introduced in (3) above is not limited to the above-described example.

For example, the transmitter 114 may stop transmission of the compression-encoded first RAW image data or the compression-encoded second RAW image data on the basis of a wireless transmission state. When the transmitter 114 stops transmission of one of the compression-encoded first RAW image data and the compression-encoded second RAW image data on the basis of a wireless transmission state, the medical endoscope device 100 can transmit the compression-encoded RAW image data more stably.

The medical endoscope device 100 according to the first embodiment has, for example, the configuration illustrated in FIG. 6.

Note that a configuration of the medical endoscope device 100 according to the first embodiment is not limited to that illustrated in FIG. 6.

For example, the transmitter 114 may be provided in the medical endoscope device 100 according to the first embodiment as a separate body from the camera head 104. By providing the transmitter 114 as a separate body from other constituent elements such as the camera head 104, substitution (so-called replacement) of the transmitter 114 can be easier. Thus, by providing the transmitter 114 as a separate body from other constituent elements, the medical endoscope device 100 can change, for example, reliability in communication, a communication distance, a transmission capacity (communication speed), an error correction method, a communication method, and the like more flexibly. That is, if the medical endoscope device 100 has a replaceable transmitter 114, for example, version upgrade for hardware relating to communication becomes easier, and thus the medical endoscope device 100 can respond to the evolution of communication more flexibly.

[3-1-2] Configuration of Medical Reception Device 200 According to First Embodiment The medical reception device 200 includes, for example, a receiver 210 and a signal processing circuit 212.

In addition, the medical reception device 200 may further include, for example, a recording medium (not illustrated) on which data to be used by the signal processing circuit 212 in processes is recorded. As the recording medium (not illustrated), for example, a flash memory, a ROM, or the like is exemplified. Note that the recording medium (not illustrated) may be an external recording medium of the medical reception device 200.

[3-1-2-1] Receiver 210

The receiver 210 is a circuit that functions as a reception unit of the medical reception device 200 and wirelessly receives compression-encoded RAW image data.

As the receiver 210, for example, a communication device compatible with wireless communication of an arbitrary communication method corresponding to the transmitter 114 included in the medical endoscope device 100 is exemplified. Note that the medical reception device 200 can also include a communication device compatible with wired communication of an arbitrary communication method, such as an optical communication device (for wired communication) or a LAN terminal and a transmission/reception circuit, as will be described below.

[3-1-2-2] Signal Processing Circuit 212

The signal processing circuit 212 is a circuit that functions as a signal processing unit of the medical reception device 200 and processes received compression-encoded RAW image data.

The signal processing circuit 212 performs, for example, a decoding process of decoding compression-encoded RAW image data. In addition, the signal processing circuit 212 performs a demosaic process on decoded RAW image data. Furthermore, the signal processing circuit 212 may perform various processes that can be performed on medical captured images such as enlargement or reduction of images relating to the electronic zoom function and inter-pixel correction.

The medical reception device 200 according to the first embodiment has, for example, the configuration illustrated in FIG. 6.

Note that a configuration of the medical reception device 200 according to the first embodiment is not limited to the example illustrated in FIG. 6. For example, a communication device for performing communication with an external device such as the display device 300 may be further included as described above. The signal processing circuit 212 controls display of the display device 300 through, for example, transmission to the display device 300 via the communication device (not illustrated).

Figure 7:
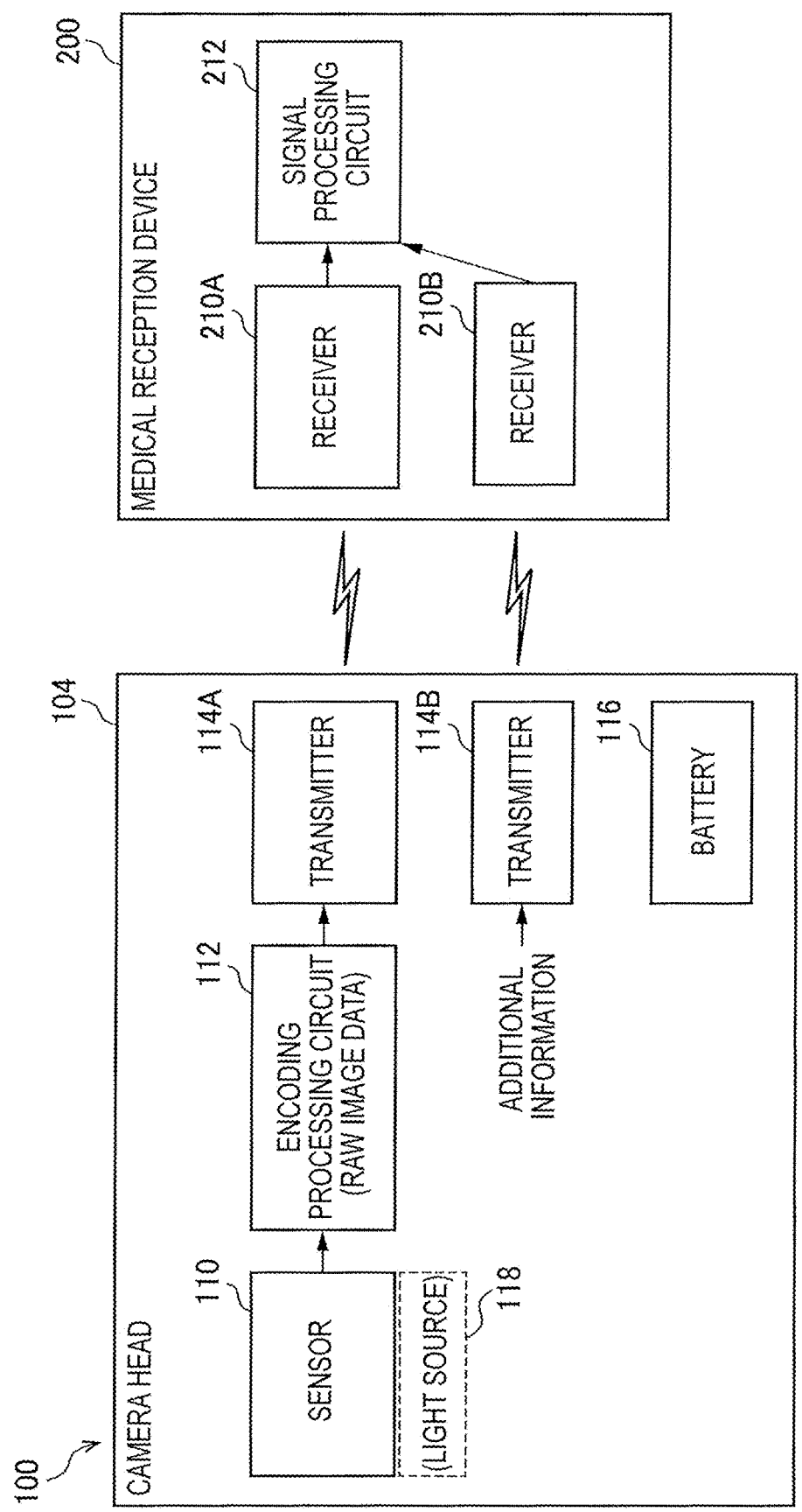
FIG. 7 is a diagram of hardware blocks illustrating an example of a configuration of a medical endoscope device and a medical reception device according to a second embodiment of the present disclosure.

[3-2] Configuration of Medical Endoscope Device and Medical Reception Device According to Second Embodiment FIG. 7 is a diagram of hardware blocks illustrating an example of a configuration of a medical endoscope device 100 and a medical reception device 200 according to a second embodiment. In FIG. 7, a hardware configuration of a camera head 104 included in the medical endoscope device 100 is illustrated, as in FIG. 6.

[3-2-1] Configuration of Medical Endoscope Device 100 According to Second Embodiment The camera head 104 of the medical endoscope device 100 includes, for example, a sensor 110, an encoding processing circuit 112, transmitters 114A and 114B, a battery 116, and a light source 118.

When the camera head 104 illustrated in FIG. 7 is compared with the camera head 104 according to the first embodiment illustrated in FIG. 6, the camera head 104 illustrated in FIG. 7 has a difference of including two transmitters. In addition, configurations and functions of the sensor 110, the encoding processing circuit 112, the battery 116, and the light source 118 illustrated in FIG. 7 are similar to those of the encoding processing circuit 112, the battery 116, and the light source 118 illustrated in FIG. 6.

The transmitter 114A is a circuit that functions as a transmission unit in the medical endoscope device 100 and wirelessly transmits compression-encoded RAW image data transferred from the encoding processing circuit 112, similarly to the transmitter 114 illustrated in FIG. 6.

The transmitter 114B is another circuit that functions as a transmission unit in the medical endoscope device 100 and transmits additional information. As additional information according to present embodiment, arbitrary data other than RAW image data, for example, one or both of control information including control commands in accordance with operations with respect to an operation device (not illustrated) included in the medical endoscope device 100 and remaining amount information indicating a remaining amount of the battery 116, or the like is exemplified.

The medical endoscope device 100 according to the second embodiment has, for example, the configuration illustrated in FIG. 7.

Note that a configuration of the medical endoscope device 100 according to the second embodiment is not limited to the example illustrated in FIG. 7.

For example, in the medical endoscope device 100 according to the second embodiment, one or both of the transmitters 114A and 114B may be provided as a separated body from the camera head 104, similarly to the medical endoscope device 100 according to the first embodiment.

In addition, the transmitter 114B may transmit additional information in wired communication of an arbitrary communication method.

[3-2-2] Configuration of Medical Reception Device 200 According to Second Embodiment The medical reception device 200 includes, for example, receivers 210A and 210B, and a signal processing circuit 212.

When the medical reception device 200 illustrated in FIG. 7 is compared with the medical reception device 200 according to the first embodiment illustrated in FIG. 6, the medical reception device 200 illustrated in FIG. 7 has a difference of including two receivers. In addition, functions and configurations of the signal processing circuit 212 illustrated in FIG. 7 are similar to functions and configurations of the signal processing circuit 212 illustrated in FIG. 6.

The receiver 210A is a circuit that functions as a reception unit in the medical reception device 200 and wirelessly receives compression-encoded RAW image data, similarly to the receiver 210 illustrated in FIG. 6. As the receiver 210A, a communication device compatible with the transmitter 114A included in the medical endoscope device 100 is exemplified.

The receiver 210B is another circuit that functions as a reception unit in the medical reception device 200 and wirelessly receives additional information. As the receiver 210B, a communication device compatible with the transmitter 114B included in the medical endoscope device 100 is exemplified.

The medical reception device 200 according to the second embodiment has, for example, the configuration illustrated in FIG. 7.

Note that a configuration of the medical reception device 200 according to the second embodiment is not limited to the example illustrated in FIG. 7.

The medical reception device 200 according to the second embodiment may further include, for example, a communication device for communicating with an external device such as the display device 300, similarly to the medical reception device 200 according to the first embodiment.

In addition, the transmitter 114B may receive, for example, additional information in wired communication of an arbitrary communication method.

Figure 8:
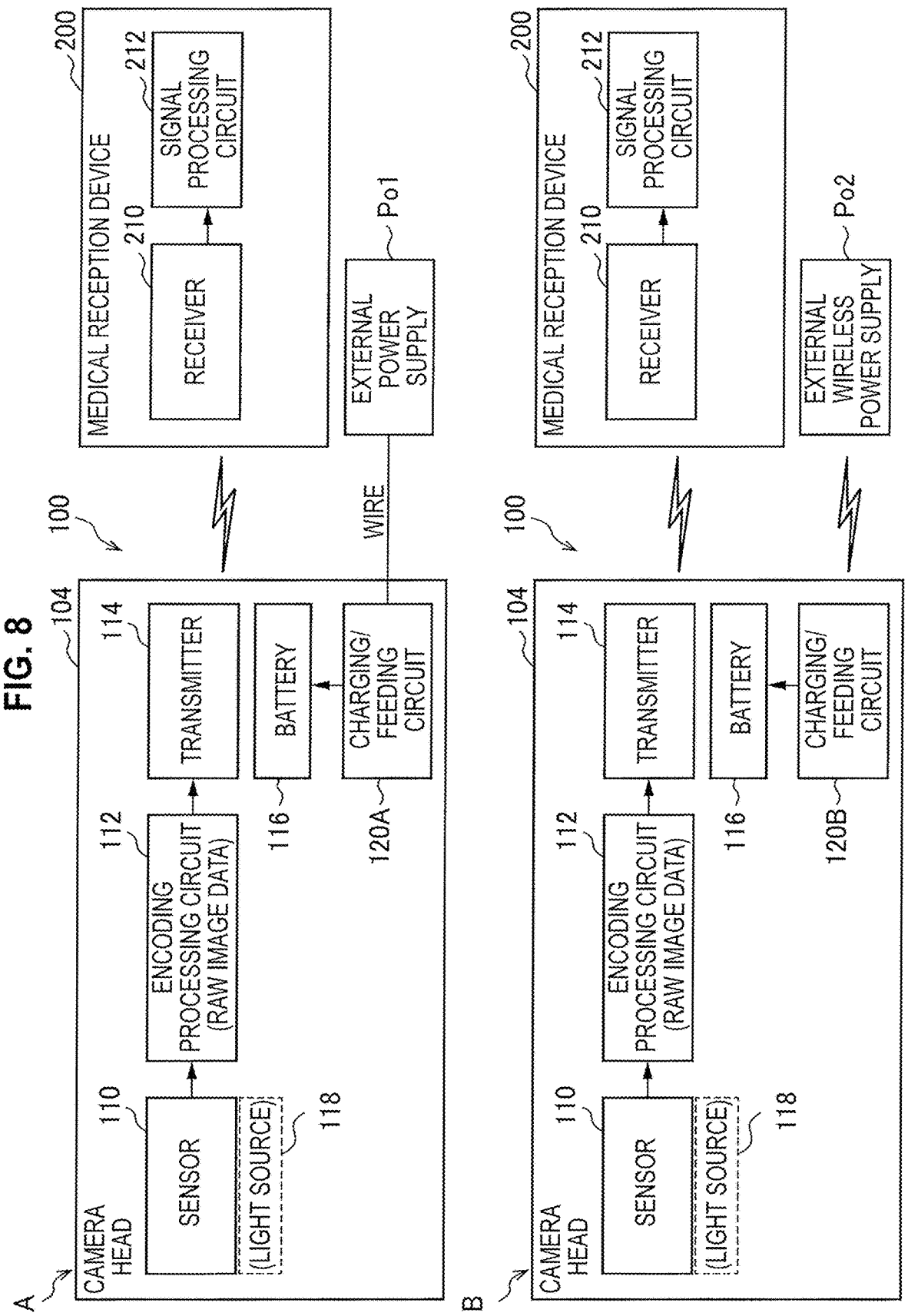
FIG. 8 is a diagram of hardware blocks illustrating an example of a configuration of a medical endoscope device and a medical reception device according to a third embodiment of the present disclosure.

[3-3] Configuration of Medical Endoscope Device and Medical Reception Device According to Third Embodiment FIG. 8 is a diagram of hardware blocks illustrating an example of configurations of medical endoscope devices 100 and medical reception devices 200 according to a third embodiment. In FIG. 8, hardware configurations of camera heads 104 included in the medical endoscope device 100 are illustrated, as in FIG. 6. In addition, external power supplies Po1 and Po2 are also illustrated in FIG. 8.

[3-3-1] Configuration of Medical Endoscope Device 100 According to Third Embodiment The camera head 104 included in the medical endoscope device 100 illustrated in A of FIG. 8 includes, for example, a sensor 110, an encoding processing circuit 112, a transmitter 114, a battery 116, a light source 118, and a charging/feeding circuit 120A.

In addition, the camera head 104 included in the medical endoscope device 100 illustrated in B of FIG. 8 includes, for example, a sensor 110, an encoding processing circuit 112, a transmitter 114, a battery 116, a light source 118, and a charging/feeding circuit 120B.

When the camera heads 104 illustrated in A and B of FIG. 8 are compared with the camera head 104 according to the first embodiment illustrated in FIG. 6, there is a difference that the camera heads 104 in A and B of FIG. 8 have the charging/feeding circuit 120A and the charging/feeding circuit 120B. In addition, functions and configurations of the sensors 110, the encoding processing circuits 112, the transmitters 114, the batteries 116, and the light sources 118 illustrated in FIG. 8 are similar to those of the encoding processing circuit 112, the transmitter 114, the battery 116, and the light source 118 illustrated in FIG. 6.

Each of the charging/feeding circuits 120A and 120B is a circuit with a function of charging the battery 116 with power supplied from an external power supply. The charging/feeding circuit 120A charges the battery 116 with power supplied from a wire-connected external power supply Po1. In addition, the charging/feeding circuit 120B charges the battery 116 with power supplied from a wirelessly connected external power supply Po2.

In addition, each of the charging/feeding circuits 120A and 120B may have a function of supplying power accumulated in the battery 116 to an external device.

The medical endoscope device 100 according to the third embodiment has, for example, the configuration illustrated in FIG. 8.

Note that a configuration of the medical endoscope device 100 according to the third embodiment is not limited to the example illustrated in FIG. 8. For example, the medical endoscope device 100 according to the third embodiment may be provided with the transmitters 114 as a separated body from the camera heads 104, similarly to the medical endoscope device 100 according to the first embodiment.

[3-3-2] Configuration of Medical Reception Device 200 According to Third Embodiment The medical reception devices 200 each include, for example, receivers 210 and signal processing circuits 212. Functions and configurations of the receivers 210 and the signal processing circuits 212 illustrated in FIG. 8 are similar to those of the receiver 210 and the signal processing circuit 212 illustrated in FIG. 6.

The medical reception device 200 according to the third embodiment has, for example, the configuration illustrated in FIG. 8.

Note that a configuration of the medical reception device 200 according to the third embodiment is not limited to the example of FIG. 8. For example, the medical reception device 200 according to the third embodiment may further include a communication device for communicating with an external device such as the display device 300, similarly to the medical reception device 200 according to the first embodiment.

Figure 9:
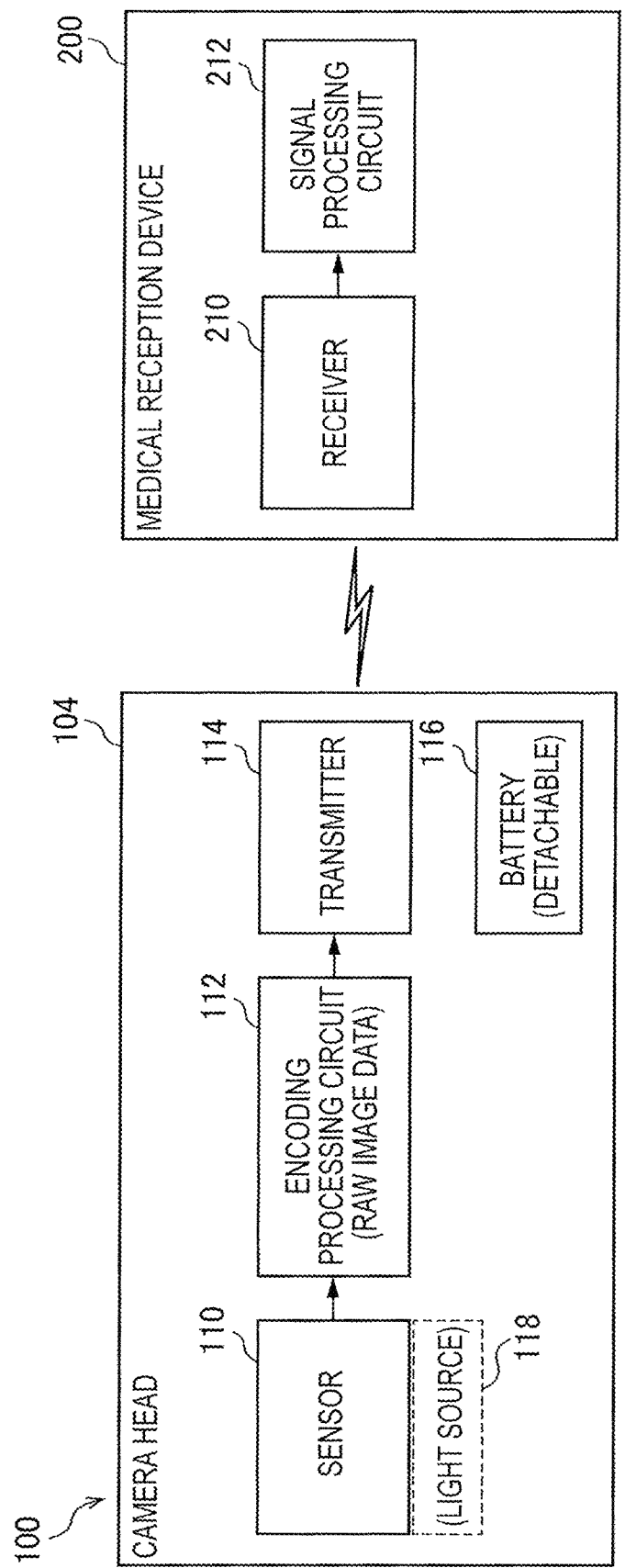
FIG. 9 is a diagram of hardware blocks illustrating an example of a configuration of a medical endoscope device and a medical reception device according to a fourth embodiment of the present disclosure.

[3-4] Configuration of Medical Endoscope Device and Medical Reception Device According to Fourth Embodiment FIG. 9 is a diagram of hardware blocks illustrating an example of configurations of a medical endoscope device 100 and a medical reception device 200 according to a fourth embodiment. In FIG. 9, a hardware configuration of a camera head 104 included in the medical endoscope device 100 is illustrated, as in FIG. 6.

[3-4-1] Configuration of Medical Endoscope Device 100 According to Fourth Embodiment The camera head 104 included in the medical endoscope device 100 includes, for example, a sensor 110, an encoding processing circuit 112, a transmitter 114, a battery 116, and a light source 118.

When the camera head 104 illustrated in FIG. 9 is compared with the camera head 104 according to the first embodiment illustrated in FIG. 6, there is a difference that the battery 116 included in the camera head 104 illustrated in FIG. 9 is detachable. In addition, functions and configurations of the sensor 110, the encoding processing circuit 112, the transmitter 114, the battery 116, and the light source 118 illustrated in FIG. 9 are similar to those of the encoding processing circuit 112, the transmitter 114, the battery 116, and the light source 118 illustrated in FIG. 6.

The medical endoscope device 100 according to the fourth embodiment has, for example, the configuration illustrated in FIG. 9.

Note that, a configuration of the medical endoscope device 100 according to the fourth embodiment is not limited to the example illustrated in FIG. 9. For example, the medical endoscope device 100 according to the fourth embodiment may be provided with the transmitter 114 a separate body from the camera head 104, similarly to the medical endoscope device 100 according to the first embodiment.

[3-4-2] Configuration of Medical Reception Device 200 According to Fourth Embodiment The medical reception device 200 includes, for example, a receiver 210 and a signal processing circuit 212. Configurations and functions of the receiver 210 and the signal processing circuit 212 illustrated in FIG. 9 are similar to those of the receiver 210 and the signal processing circuit 212 illustrated in FIG. 6.

The medical reception device 200 according to the fourth embodiment has, for example, the configuration illustrated in FIG. 9.

Note that a configuration of the medical reception device 200 according to the fourth embodiment is not limited to the example illustrated in FIG. 9. For example, the medical reception device 200 according to the fourth embodiment may further include a communication device for communicating with an external device such as the display device 300, similarly to the medical reception device 200 according to the first embodiment.

Figure 10:
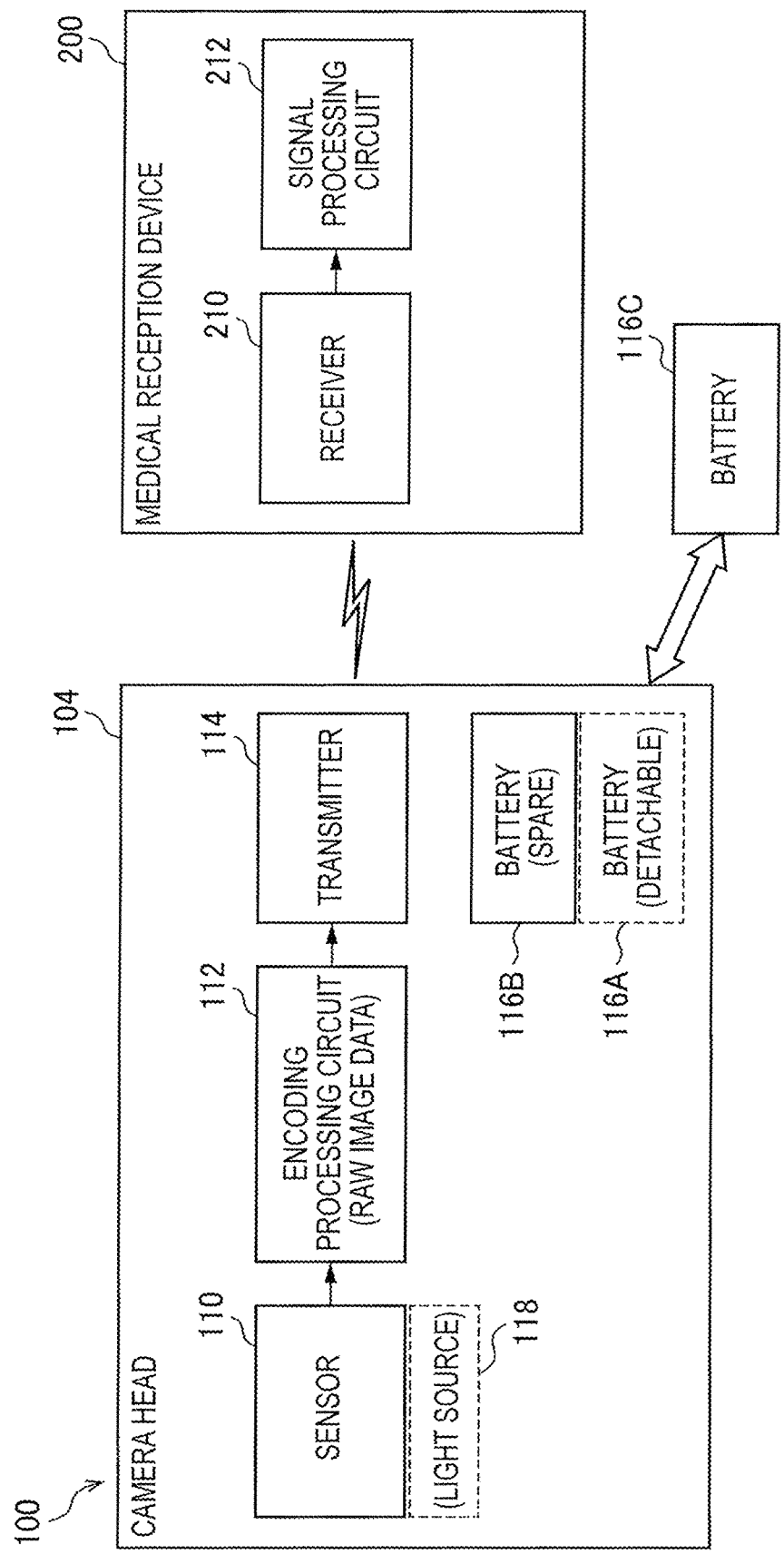
FIG. 10 is a diagram of hardware blocks illustrating an example of a configuration of a medical endoscope device and a medical reception device according to a fifth embodiment of the present disclosure.

[3-5] Configuration of Medical Endoscope Device and Medical Reception Device According to Fifth Embodiment FIG. 10 is a diagram of hardware blocks illustrating an example of configurations of a medical endoscope device 100 and a medical reception device 200 according to a fifth embodiment. In FIG. 10, a hardware configuration of a camera head 104 included in the medical endoscope device 100 is illustrated, as in FIG. 6. In addition, in FIG. 10, a battery 16C that can be attached to the camera head 104 is illustrated together.

[3-5-1] Configuration of Medical Endoscope Device 100 According to Fifth Embodiment The camera head 104 included in the medical endoscope device 100 includes, for example, a sensor 110, an encoding processing circuit 112, a transmitter 114, batteries 116A and 116B, and a light source 118.

When the camera head 104 illustrated in FIG. 10 is compared with the camera head 104 according to the first embodiment illustrated in FIG. 6, there is a difference that the camera head 104 illustrated in FIG. 10 includes two batteries. In addition, configurations and functions of the sensor 110, the encoding processing circuit 112, the transmitter 114, and the light source 118 illustrated in FIG. 10 are similar to those of the encoding processing circuit 112, the transmitter 114, and the light source 118 illustrated in FIG. 6.

The battery 116A is detachable from the camera head 104, similarly to the battery 116 included in the camera head 104 according to the fourth embodiment illustrated in FIG. 9. That is, in the camera head 104 illustrated in FIG. 10, the battery 116A and the battery 116C are interchangeable.

The battery 116B is a spare battery included in the camera head 104. Since the camera head 104 includes the battery 116B, the medical endoscope device 100 can replace a battery while operating. In addition, since the camera head 104 includes the battery 116B, a drive time of the medical endoscope device 100 can be extended.

The medical endoscope device 100 according to the fifth embodiment has, for example, the configuration illustrated in FIG. 10.

Note that a configuration of the medical endoscope device 100 according to the fifth embodiment is not limited to the example illustrated in FIG. 10. For example, the medical endoscope device 100 according to the fifth embodiment may be provided with the transmitter 114 as a separate body from the camera head 104, similarly to the medical endoscope device 100 according to the first embodiment.

[3-5-2] Configuration of Medical Reception Device 200 According to the Fifth Embodiment The medical reception device 200 includes, for example, a receiver 210 and a signal processing circuit 212. Configurations and functions of the receiver 210 and the signal processing circuit 212 illustrated in FIG. 10 are similar to those of the receiver 210 and the signal processing circuit 212 illustrated in FIG. 6.

The medical reception device 200 according to the fifth embodiment has, for example, the configuration illustrated in FIG. 10.

Note that a configuration of the medical reception device 200 according to the fifth embodiment is not limited to the example illustrated in FIG. 10. For example, the medical reception device 200 according to the fifth embodiment may further include a communication device for communicating with an external device such as the display device 300, similarly to the medical reception device 200 according to the first embodiment.

Figure 11:
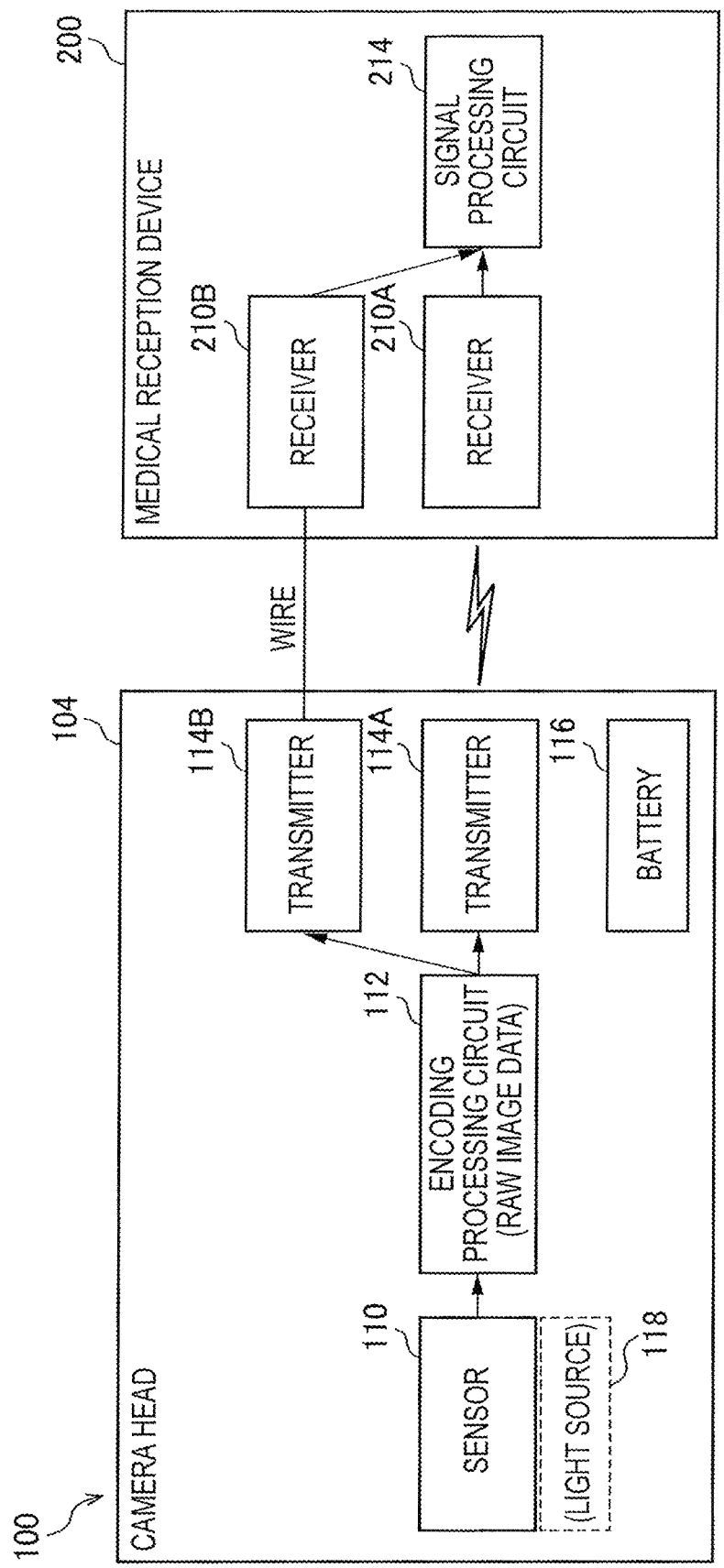
FIG. 11 is a diagram of hardware blocks illustrating an example of a configuration of a medical endoscope device and a medical reception device according to a sixth embodiment of the present disclosure.

[3-6] Configuration of Medical Endoscope Device and Medical Reception Device According to Sixth Embodiment FIG. 11 is a diagram of hardware blocks illustrating an example of configurations of a medical endoscope device 100 and a medical reception device 200 according to a sixth embodiment. In FIG. 11, a hardware configuration of a camera head 104 included in the medical endoscope device 100 is illustrated, as in FIG. 6.

[3-6-1] Configuration of Medical Endoscope Device 100 According to Sixth Embodiment The camera head 104 included in the medical endoscope device 100 includes, for example, a sensor 110, an encoding processing circuit 112, transmitters 114A and 114B, a battery 116, and a light source 118.

When the camera head 104 illustrated in FIG. 11 is compared with the camera head 104 according to the first embodiment illustrated in FIG. 6, there is a difference that the camera head 104 illustrated in FIG. 11 includes two transmitters. In addition, configurations and functions of the sensor 110, the encoding processing circuit 112, the battery 116, and the light source 118 illustrated in FIG. 11 are similar to those of the encoding processing circuit 112, the battery 116, and the light source 118 illustrated in FIG. 6.

The transmitter 114A is a circuit that functions as a transmission unit in the medical endoscope device 100, and wirelessly transmits compression-encoded RAW image data transferred from the encoding processing circuit 112, similarly to the transmitter 114 illustrated in FIG. 6.

The transmitter 114B is another circuit that functions as a transmission unit in the medical endoscope device 100, and transmits compression-encoded RAW image data transferred from the encoding processing circuit 112 in a wired manner.

The medical endoscope device 100 according to the sixth embodiment has, for example, the configuration illustrated in FIG. 11. With the configuration illustrated in FIG. 11, for example, even in an environment in which it is difficult to wirelessly transmit compression-encoded RAW image data, the medical endoscope device 100 can transmit the compression-encoded RAW image data in arbitrary wired communication.

Note that a configuration of the medical endoscope device 100 according to the sixth embodiment is not limited to the example illustrated in FIG. 11. For example, the medical endoscope device 100 according to the sixth embodiment may be provided with one or both of the transmitters 114A and 114B as a separate body from the camera head 104, similarly to the medical endoscope device 100 according to the first embodiment.

[3-6-2] Configuration of Medical Reception Device 200 According to Sixth Embodiment The medical reception device 200 includes, for example, receivers 210A and 210B, and a signal processing circuit 214.

When the medical reception device 200 illustrated in FIG. 11 is compared with the medical reception device 200 according to the first embodiment illustrated in FIG. 6, there are differences that the medical reception device 200 illustrated in FIG. 11 has two receivers and the signal processing circuit 214 has a different function.

The receiver 210A is a circuit that functions as a reception unit in the medical reception device 200, and wirelessly receives compression-encoded RAW image data, similarly to the receiver 210 illustrated in FIG. 6. As the receiver 210A, a communication device corresponding to the transmitter 114A included in the medical endoscope device 100 is exemplified.

The receiver 210B is another circuit that functions as a reception unit in the medical reception device 200, and receives compression-encoded RAW image data in a wired manner. As the receiver 210B, a communication device corresponding to the transmitter 114B included in the medical endoscope device 100 is exemplified.

The signal processing circuit 214 processes compression-encoded RAW image data received by the receiver 210A or compression-encoded RAW image data received by the receiver 210B. The signal processing circuit 214 processes received compression-encoded RAW image data, similarly to the signal processing circuit 212 according to the first embodiment illustrated in FIG. 6.

Here, the signal processing circuit 214 performs processes at each set predetermined period, for example. The predetermined period may be a preset fixed period or a variable period that can be changed in accordance with an operation with respect to an operation device such as a remote controller, or the like. In addition, the signal processing circuit 214 processes either RAW image data first transferred at a process start timing of compression-encoded RAW image data transferred from the receiver 210A and compression-encoded RAW image data transferred from the receiver 210B.

Note that an example of a process performed by the signal processing circuit 214 is not limited to the above-described example. For example, the signal processing circuit 214 may process RAW image data of the compression-encoded RAW image data transferred at the process start timing with a higher signal level.

The medical reception device 200 according to the sixth embodiment has, for example, the configuration illustrated in FIG. 11.

Note that a configuration of the medical reception device 200 according to the sixth embodiment is not limited to the example illustrated in FIG. 11. For example, the medical reception device 200 according to the sixth embodiment may further include a communication device for communicating with an external device such as the display device 300, similarly to the medical reception device 200 according to the first embodiment.

Figure 12:
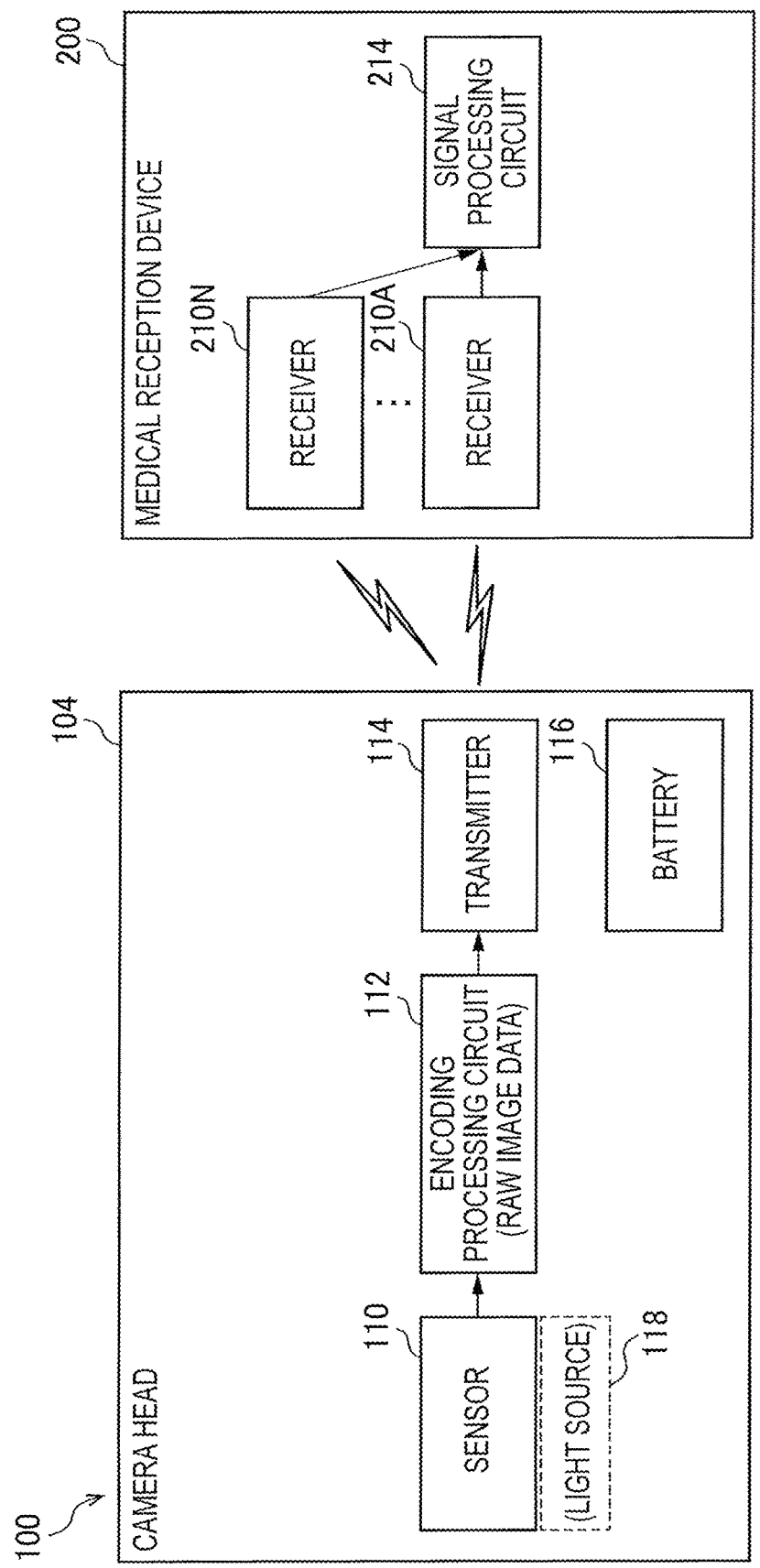
FIG. 12 is a diagram of hardware blocks illustrating an example of a configuration of a medical endoscope device and a medical reception device according to a seventh embodiment of the present disclosure.

[3-7] Configuration of Medical Endoscope Device and Medical Reception Device According to Seventh Embodiment FIG. 12 is a diagram of hardware blocks illustrating an example of configurations of a medical endoscope device 100 and a medical reception device 200 according to a seventh embodiment. In FIG. 12, a hardware configuration of a camera head 104 included in the medical endoscope device 100 is illustrated, as in FIG. 6.

[3-7-1] Configuration of Medical Endoscope Device 100 According to Seventh Embodiment The camera head 104 included in the medical endoscope device 100 includes, for example, a sensor 110, an encoding processing circuit 112, a transmitter 114, a battery 116, and a light source 118.

Functions and configurations of the sensor 110, the encoding processing circuit 112, the transmitter 114, the battery 116, and the light source 118 illustrated in FIG. 12 are similar to those of the encoding processing circuit 112, the transmitter 114, the battery 116, and the light source 118 illustrated in FIG. 6.

The medical endoscope device 100 according to the seventh embodiment has, for example, the configuration illustrated in FIG. 12.

Note that a configuration of the medical endoscope device 100 according to the seventh embodiment is not limited to the example illustrated in FIG. 12. For example, the medical endoscope device 100 according to the seventh embodiment may be provided with the transmitter 114 as a separate body from the camera head 104, similarly to the medical endoscope device 100 according to the first embodiment.

[3-7-2] Configuration of Medical Reception Device 200 According to Seventh Embodiment The medical reception device 200 includes, for example, receivers 210A, . . . , and 210N, and a signal processing circuit 214.

When the medical reception device 200 illustrated in FIG. 12 is compared with the medical reception device 200 according to the first embodiment illustrated in FIG. 6, there is a difference that the medical reception device 200 illustrated in FIG. 12 has two or more receivers and the signal processing circuit 214 has a different function.

Each of the receivers 210A, . . . , and 210N is a circuit that functions as a reception unit in the medical reception device 200 and wirelessly receives compression-encoded RAW image data, similarly to the receiver 210 illustrated in FIG. 6. As each of the receivers 210A, . . . , and 210N, a communication device corresponding to the transmitter 114A included in the medical endoscope device 100 is exemplified.

The signal processing circuit 214 processes any RAW image data of compression-encoded RAW image data received by each of the receivers 210A, . . . , and 210N. The signal processing circuit 214 processes any RAW image data of compression-encoded RAW image data received by each of the receivers 210A, . . . , and 210N, for example, similarly to the signal processing circuit 214 according to the sixth embodiment illustrated in FIG. 11.

The medical reception device 200 according to the seventh embodiment has, for example, the configuration illustrated in FIG. 12. Since the medical reception device 200 includes the plurality of receivers, radio wave environments for transmission and reception of compression-encoded RAW image data can be improved.

Note that, a configuration of the medical reception device 200 according to the seventh embodiment is not limited to the example illustrated in FIG. 12.

For example, the medical reception device 200 according to the seventh embodiment may further include a communication device for communicating with an external device such as the display device 300, similarly to the medical reception device 200 according to the first embodiment.

In addition, the medical reception device 200 according to the seventh embodiment may also can process compression-encoded RAW image data received using an external antenna. The signal processing circuit 214 processes, for example, compression-encoded RAW image data received using the included receivers or compression-encoded RAW image data received using an external antenna. In this case, the medical reception device 200 according to the seventh embodiment may not include a plurality of receivers.

External antennas can be provided in various places in the medical sites, for example, trocars, beds, shadowless light, and the like.

[4] Example of Effects Exhibited when Medical Observation Systems According to Present Embodiment is Used The following effects, for example, can be exhibited when the medical observation systems according to the present embodiments are used. Note that, it is a matter of course that effects to be exhibited when the medical observation systems according to the present embodiments are used are not limited to the following examples.

A size of data to be transmitted can be further reduced by compression-encoding RAW image data. Thus, a low transmission speed or low-compressed high image quality is realized.

Since medical captured images can be compression-encoded by smaller predetermined units by using the compression-encoding method according to the present embodiments, for example, compression with lower latency in which the delay time is far shorter than 1 [msec] can be realized.

Since compression-encoded RAW image data is wirelessly transmitted, it is possible to perform image processing such as the demosaic process in a reception side device. That is, it is not necessary for a medical endoscope device (a transmission side device) having a camera head to include a signal processing circuit that performs the demosaic process. Therefore, power consumption of the medical endoscope device (a transmission side device) having the camera head can be further reduced.

Since power consumption of the medical endoscope device is further reduced and it is not necessary to include a signal processing circuit that performs the demosaic process, for example, miniaturization of the size of a battery and miniaturization and a light weight of the camera head can be achieved.

Although the medical endoscope device (a transmission side device) having the camera head is demanded to achieve lower power consumption, miniaturization, and heating prevention, for example, the demands can be satisfied more easily if the medical observation systems according to the present embodiments is used.

(Program According to Present Embodiments)

When a program for causing a computer to function as the medical endoscope device according to the present embodiments (e.g., a program for causing the computer to function as an encoding processing unit and a transmission unit, in other words, a program by which the processes of the transmission methods according to the present embodiments can be executed) is executed by a processor of the computer or the like, image data indicating a compression-encoded medical captured image can be transmitted with low latency.

In addition, when the program for causing a computer to function as the medical endoscope devices according to the present embodiments is executed by a processor of the computer or the like, effects exhibited by performing the processes of the above-described transmission methods according to the present embodiments can be exhibited.

It should be understood by those skilled in the art that various modifications, combinations, sub-combinations and alterations may occur depending on design requirements and other factors insofar as they are within the scope of the appended claims or the equivalents thereof.

Although it has been described above that, for example, the program (computer program) for causing the computer to function as the medical endoscope devices according to the present embodiments is provided, the present embodiments can also provide a recording medium in which the program is stored therealong.

The above-described configurations are examples of the present embodiments, and of course belong to the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical endoscope device including:

an encoding processing unit configured to compression-encode RAW image data of a medical captured image of an observation target captured by an imaging device that is inserted into a body of a patient and captures an image of an inside of the body; and a transmission unit configured to wirelessly transmit the compression-encoded RAW image data.

(2) The medical endoscope device according to (1), in which the encoding processing unit compression-encodes the RAW image data at a plurality of different compression ratios, and the transmission unit transmits the compression-encoded RAW image data corresponding to a wireless transmission state, of the RAW image data compression-encoded at the plurality of compression ratios.

(3) The medical endoscope device according to (1), in which the transmission unit trsnsmits the compression-encoded RAW image data at different frequencies.

(4) The medical endoscope device according to (3), in which the transmission unit transmits the compression-encoded RAW image data at different frequencies at a same time.

(5) The medical endoscope device according to (3), in which the transmission unit transmits the compression-encoded RAW image data at one of a plurality of frequencies.

(6) The medical endoscope device according to (5), in which the transmission unit transmits the compression-encoded RAW image data at a frequency corresponding to a wireless transmission state.

(7) The medical endoscope device according to (5) or (6), in which the transmission unit transmits the compression-encoded RAW image data at a frequency corresponding to an operation state of a predetermined medical apparatus.

(8) The medical endoscope device according to any one of (1) to (7), in which the encoding processing unit performs compression-encoding at a compression ratio corresponding to a state of electronic zoom of the imaging device.

(9) The medical endoscope device according to (1), in which the encoding processing unit compression-encodes each of first RAW image data of a medical captured image for a right eye and second RAW image data of a medical captured image for a left eye, and the transmission unit wirelessly transmits each of the compression-encoded first RAW image data and the compression-encoded second RAW image data.

(10) The medical endoscope device according to (9), in which the transmission unit stops transmission of the compression-encoded first RAW image data or the compression-encoded second RAW image data on a basis of a wireless transmission state.

(11) The medical endoscope device according to any one of (1) to (10), in which the transmission unit further transmits additional information.

(12) The medical endoscope device according to (1), in which the encoding processing unit changes a way of compression-encoding of the RAW image data on a basis of a wireless transmission state.

(13) The medical endoscope device according to any one of (1) to (12), in which the transmission unit further transmits the compression-encoded RAW image data in a wired manner.

(14) The medical endoscope device according to any one of (1) to (13), in which the encoding processing unit compression-encodes the RAW image data by a predetermined unit that is smaller than the medical captured image, and the transmission unit transmits the RAW image data compression-encoded by the predetermined unit.

(15) The medical endoscope device according to any one of (1) to (14), in which the encoding processing unit compression-encodes the RAW image data without performing a demosaic process.

(16) A medical reception device including:
a reception unit configured to wirelessly receive compression-encoded RAW image data obtained by compression-encoding RAW image data of a medical captured image of an observation target captured by an imaging device that is inserted into a body of a patient and captures an image of an inside of the body; and
a signal processing unit configured to process the received compression-encoded RAW image data.

(17) The medical reception device according to (16), in which the signal processing unit processes the compression-encoded RAW image data received by the reception unit or the compression-encoded RAW image data received by an external antenna.

(18) A medical observation system including:
a medical endoscope device including
an encoding processing unit configured to compression-encode RAW image data of a medical captured image of an observation target captured by an imaging device that is inserted into a body of a patient and captures an image of an inside of the body, and
a transmission unit configured to wirelessly transmit the compression-encoded RAW image data; and
a medical reception device including
a reception unit configured to wirelessly receive the compression-encoded RAW image data, and
a signal processing unit configured to process the received compression-encoded RAW image data.

(19) The medical observation system according to (18),
in which the encoding processing unit of the medical endoscope device compression-encodes the RAW image data without performing a demosaic process, and
the signal processing unit of the medical reception device performs the demosaic process on the compression-encoded RAW image data received by the reception unit or the compression-encoded RAW image data received by an external antenna.

What is claimed is:

1. A surgical system, comprising:
an imaging device including an image sensor configured to capture a medical image of an observation target and output RAW image data of the medical image;
circuitry configured to
compression-encode the RAW image data of the medical image of the observation target captured by the imaging device at a plurality of different compression ratios, and
wirelessly transmit, using a transmitter, simultaneously and at a plurality of different frequencies, the compression-encoded RAW image data; and
a receiving device including
a receiver configured to receive the compression-encoded RAW image data transmitted from the transmitter; and
a decoder configured to decode the compression-encoded RAW image data.

2. The surgical system according to claim 1, wherein the circuitry is configured to change a way of compression-encoding the RAW image data based on a wireless transmission state.

3. The surgical system according to claim 2, wherein the circuitry is configured to change the way of compression-encoding the RAW image data based on the wireless transmission state, by changing a compression ratio used to compression-encode the RAW image data to a compression ratio corresponding to the wireless transmission state.

4. The surgical system according to claim 2, wherein the circuitry is configured to change the way of compression-encoding the RAW image data based on the wireless transmission state, by changing a predetermined unit used to compression-encode the RAW image data to a unit corresponding to the wireless transmission state.

5. The surgical system according to claim 2, wherein the circuitry is configured to change the way of compression-encoding the RAW image data based on the wireless transmission state, by switching whether an error correction code is to be added in accordance with the wireless transmission state.

6. The surgical system according to claim 2, wherein the circuitry is configured to change the way of compression-encoding the RAW image data based on the wireless transmission state, by referring to a table stored in a memory.

7. The surgical system according to claim 6, wherein each of a plurality of wireless transmission states is associated with data indicating a way of compression-encoding in the table.

8. The surgical system according to claim 2, wherein the circuitry is configured to specify the wireless transmission state, based on a result of bidirectional communication with the receiving device.

9. The surgical system according to claim 1, wherein the circuitry is configured to compression-encode the RAW image data at a compression ratio corresponding to a state of electronic zoom of the imaging device.

10. The surgical system according to claim 1, wherein
the circuitry is configured to compression-encode each of first RAW image data of the medical image for a right eye and second RAW image data of the medical image for a left eye, and
the transmitter wirelessly transmits each of the compression-encoded first RAW image data and the compression-encoded second RAW image data.

11. The surgical system according to claim 10, wherein the transmitter stops transmission of the compression-encoded first RAW image data or the compression-encoded second RAW image data based on a wireless transmission state.

12. The surgical system according to claim 1, wherein the transmitter further transmits additional information.

13. The surgical system according to claim 1, wherein the transmitter further transmits the compression-encoded RAW image data in a wired manner.

14. The surgical system according to claim 1, wherein the circuitry is configured to compression-encode the RAW image data without performing a demosaic process.

15. The surgical system according to claim 1, wherein the circuitry is further configured to:
store, in a memory, a plurality of frequencies, each of the plurality of the frequencies corresponding to each frequency of each of a plurality of predetermined medical apparatuses in an operation state thereof, each of the plurality of the frequencies being over zero frequency, the plurality of the predetermined medical apparatuses being different from the medical endoscope device;

identify, from among the predetermined medical apparatuses, medical apparatuses that are in the operation state; and identify, based on the plurality of the frequencies stored in the memory, a frequency in accordance with the operation states of the predetermined medical apparatuses, and the transmitter is configured to wirelessly transmit the compression-encoded RAW image data at the identified frequency.

16. The surgical system according to claim 15, wherein the predetermined medical apparatus is an electrical scalpel or bipolar forceps.

17. The surgical system according to claim 15, wherein the circuitry is configured to:

receive, from the predetermined medical apparatuses, information regarding the operation states of the predetermined medical apparatuses; and identify, from among the plurality of the frequencies, the frequency based on the received information regarding the operation states of the predetermined medical apparatuses.

18. The surgical system according to claim 17, wherein the circuitry is configured to identify, from among the plurality of the frequencies, the frequency such that the wireless transmission of the compression-encoded RAW image data by the transmitter is less affected by an electric field generated by the predetermined medical apparatuses.

19. The surgical system according to claim 1, wherein the surgical system is an endoscope.

20. A medical imaging device, comprising:

an imaging device including an image sensor configured to capture a medical image of an observation target and output RAW image data of the medical image; and circuitry configured to compression-encode the RAW image data of the medical image of the observation target captured by the imaging device at a plurality of different compression ratios, and wirelessly transmit, using a transmitter, simultaneously and at a plurality of different frequencies, the compression-encoded RAW image data to a receiver.

21. The medical imaging device according to claim 20, wherein the receiving device comprises:

a receiver configured to receive the compression-encoded RAW image data transmitted from the transmitter; and a decoder configured to decode the compression-encoded RAW image data.

* * * * *